(12) United States Patent
Hajduk et al.

(10) Patent No.: US 6,393,898 B1
(45) Date of Patent: May 28, 2002

(54) HIGH THROUGHPUT VISCOMETER AND METHOD OF USING SAME

(75) Inventors: Damian Hajduk, San Jose; Paul Mansky, San Francisco, both of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/578,997

(22) Filed: May 25, 2000

(51) Int. Cl.[7] .............................................. G01N 11/06
(52) U.S. Cl. ...................... 73/54.05; 73/54.07; 73/54.08
(58) Field of Search ............................. 73/54.01, 54.02, 73/54.05, 54.07, 54.08

(56) References Cited

U.S. PATENT DOCUMENTS

| | | | | |
|---|---|---|---|---|
| 1,870,412 A | * | 8/1932 | Kennedy | 73/54.05 |
| 3,071,961 A | * | 1/1963 | Heigl et al. | 73/54.08 |
| 3,675,475 A | | 7/1972 | Weinstein | |
| 3,713,328 A | * | 1/1973 | Aritomi | 73/54.08 |
| 3,798,960 A | | 3/1974 | Glass | 73/54.05 |
| 3,805,598 A | | 4/1974 | Corcoran | |
| 3,818,751 A | | 6/1974 | Karper et al. | |
| 3,849,874 A | | 11/1974 | Jefferes | |
| 3,895,513 A | * | 7/1975 | Richardson | 73/54.07 |
| 3,908,441 A | * | 9/1975 | Virloget | 73/54.08 |
| 3,933,032 A | | 1/1976 | Tschoegl | |
| 4,229,979 A | | 10/1980 | Greenwood | |
| 4,447,125 A | | 5/1984 | Lazay et al. | |
| 4,517,830 A | * | 5/1985 | Gunn et al. | 73/54.15 |
| 4,567,774 A | | 2/1986 | Manahan et al. | |
| 4,570,478 A | | 2/1986 | Soong | 73/54.39 |
| 4,599,219 A | * | 7/1986 | Cooper et al. | 422/61 |
| 4,602,501 A | | 7/1986 | Hirata | 73/54.23 |
| 4,605,589 A | | 8/1986 | Orphanides | |
| 4,680,958 A | | 7/1987 | Ruelle et al. | 73/54.14 |
| 4,685,328 A | | 8/1987 | Huebner et al. | 73/54.04 |
| 4,699,000 A | | 10/1987 | Lashmore et al. | |
| 4,715,007 A | | 12/1987 | Fujita et al. | |
| 4,740,078 A | | 4/1988 | Daendliker et al. | |
| 4,749,854 A | | 6/1988 | Martens | |
| 4,789,236 A | | 12/1988 | Hodor et al. | |
| 4,793,174 A | | 12/1988 | Yau | 73/54.04 |
| 4,829,837 A | * | 5/1989 | Telfer | 73/863.01 |
| 4,893,500 A | | 1/1990 | Fink-Jensen | 73/54.37 |
| 4,899,575 A | | 2/1990 | Chu et al. | 73/54.08 |
| 4,899,581 A | | 2/1990 | Allen et al. | |

(List continued on next page.)

FOREIGN PATENT DOCUMENTS

| | | | | |
|---|---|---|---|---|
| JP | 02297040 A | * | 12/1990 | 73/54.05 |
| WO | WO 96/11878 | | 4/1996 | |
| WO | WO 00/17413 | | 3/2000 | |

(List continued on next page.)

OTHER PUBLICATIONS

Bowlt, C. "A Simple Capillary Viscometer" in Physics Education, Mar. 1975, Institute of Physics, vol. 10, No. 2, England, pp. 102–103.*

(List continued on next page.)

*Primary Examiner*—Hezron Williams
*Assistant Examiner*—Michael Cygan
(74) *Attorney, Agent, or Firm*—Dobrusin & Thennisch PC

(57) ABSTRACT

An apparatus and method for measuring viscosity or related properties of fluid samples in parallel is disclosed. The apparatus includes a plurality of tubes and reservoirs in fluid communication with the tubes. The tubes provide flow paths for the fluid samples, which are initially contained within the reservoirs. The apparatus also includes a mechanism for filling the reservoirs with the fluid samples, and a device for determining volumetric flow rates of fluid samples flowing from the reservoirs through the plurality of tubes simultaneously. The disclosed apparatus is capable of measuring viscosity or related properties of at least five fluid samples simultaneously. Useful reservoirs and tubes include syringes.

56 Claims, 9 Drawing Sheets

U.S. PATENT DOCUMENTS

| | | | |
|---|---|---|---|
| 4,932,270 A | 6/1990 | Lurie et al. | |
| 4,975,320 A | 12/1990 | Goldstein et al. | |
| 5,008,081 A | 4/1991 | Blau et al. | |
| 5,051,239 A | * 9/1991 | von der Goltz | 422/73 |
| 5,092,179 A | 3/1992 | Ferguson | |
| 5,115,669 A | 5/1992 | Fuller et al. | 73/54.39 |
| 5,142,900 A | 9/1992 | Duke | 73/54.39 |
| 5,193,383 A | 3/1993 | Burnham et al. | |
| 5,236,998 A | 8/1993 | Lundeen et al. | |
| 5,269,190 A | 12/1993 | Kramer et al. | |
| 5,271,266 A | 12/1993 | Eschbach | |
| 5,272,912 A | * 12/1993 | Katsuzaki | 73/54.08 |
| 5,280,717 A | 1/1994 | Hoseney et al. | |
| 5,303,030 A | 4/1994 | Abraham et al. | |
| 5,305,633 A | 4/1994 | Weissenbacher et al. | |
| 5,306,510 A | * 4/1994 | Meltzer | 422/100 |
| 5,398,885 A | 3/1995 | Andersson et al. | |
| 5,437,192 A | 8/1995 | Kawamoto et al. | |
| 5,438,863 A | 8/1995 | Johnson | |
| 5,452,614 A | 9/1995 | Kato et al. | |
| 5,452,619 A | * 9/1995 | Kawanabe et al. | 73/864.01 |
| 5,517,860 A | 5/1996 | Lin et al. | |
| 5,520,042 A | 5/1996 | Garritano et al. | |
| 5,532,942 A | 7/1996 | Kitamura et al. | |
| 5,610,325 A | 3/1997 | Rajapopal et al. | 73/54.39 |
| 5,626,779 A | 5/1997 | Okada | |
| 5,699,159 A | 12/1997 | Mason | |
| 5,700,953 A | 12/1997 | Hlady et al. | |
| 5,723,972 A | 3/1998 | Miyazaki | |
| 5,728,532 A | 3/1998 | Ackley | |
| 5,756,883 A | * 5/1998 | Forbes | 73/54.05 |
| 5,764,068 A | 6/1998 | Katz et al. | |
| 5,776,359 A | 7/1998 | Schultz et al. | |
| 5,817,947 A | 10/1998 | Bergerus | |
| 5,821,407 A | 10/1998 | Sekiguchi et al. | 73/54.28 |
| 5,847,283 A | 12/1998 | Finot et al. | |
| 5,877,428 A | 3/1999 | Scolton | |
| 5,892,157 A | 4/1999 | Syre | |
| 5,922,967 A | 7/1999 | Motoyama | |
| 5,959,297 A | 9/1999 | Weinberg et al. | |
| 5,985,356 A | 11/1999 | Schultz et al. | |
| 5,999,887 A | 12/1999 | Giannakopoulos et al. | |
| 6,004,617 A | 12/1999 | Schultz et al. | |
| 6,010,616 A | 1/2000 | Lewis et al. | |
| 6,013,199 A | 1/2000 | McFarland et al. | |
| 6,030,917 A | 2/2000 | Weinberg et al. | |
| 6,033,913 A | 3/2000 | Morozov et al. | |
| 6,034,240 A | 3/2000 | LaPointe | |
| 6,034,775 A | 3/2000 | McFarland et al. | |
| 6,040,193 A | 3/2000 | Winkler | |
| 6,043,317 A | 3/2000 | Mumick et al. | |
| 6,043,363 A | 3/2000 | LaPointe et al. | |
| 6,045,671 A | 4/2000 | Wu et al. | |
| 6,045,755 A | * 4/2000 | Lebl et al. | 422/103 |
| 6,050,138 A | 4/2000 | Lynch et al. | |
| 6,050,139 A | 4/2000 | Bousfield et al. | |
| 6,087,181 A | 7/2000 | Cong | |
| 6,092,414 A | 7/2000 | Newman | |
| 6,124,476 A | 9/2000 | Guram et al. | |
| 6,143,252 A | * 11/2000 | Haxo et al. | 422/100 |
| 6,149,882 A | 11/2000 | Guan et al. | |
| 6,151,123 A | 11/2000 | Nielson | |
| 6,157,449 A | 12/2000 | Hajduk | |
| 6,175,409 B1 | 1/2001 | Nielsen et al. | |
| 6,177,528 B1 | 1/2001 | LaPointe et al. | |
| 6,182,499 B1 | 2/2001 | McFarland et al. | |
| 6,187,164 B1 | 2/2001 | Warren et al. | |
| 6,203,726 B1 | 3/2001 | Danielson et al. | |
| 6,225,487 B1 | 5/2001 | Guram | |
| 6,225,550 B1 | 5/2001 | Hornbostel et al. | |
| 6,242,623 B1 | 6/2001 | Boussie et al. | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,265,601 B1 | 7/2001 | Guram et al. | |
| 6,268,513 B1 | 7/2001 | Guram et al. | |
| 6,294,388 B1 | 9/2001 | Petro | |
| 6,296,771 B1 | 10/2001 | Miroslav | |

FOREIGN PATENT DOCUMENTS

| | | |
|---|---|---|
| WO | WO 00/23921 | 4/2000 |
| WO | WO 00/36410 | 6/2000 |
| WO | WO 00/40331 | 7/2000 |
| WO | WO 00/51720 | 9/2000 |
| WO | WO 00/67086 | 11/2000 |

OTHER PUBLICATIONS

Calleja, F.J. Balta, "Microhardness Studies of Polymres and Their Transitions," TRIP, Dec. 1994, pp. 419–425, vol. 2, No. 12.

"DMA 2980 Dynamic Mechanical Analyzer," www.tainst-.com/dma2.html, Dec. 29, 2000.

"Introducing the New DMTA V!", www.rheometricscientific.com/dmtaV.htm, Dec. 29, 2000.

Lacombe, Robert H. and Jeremy Greenblatt, "Mechanical Properties of Thin Polyimide Films," pp. 647–668.

Sadovsky, Ella Amitay and H. Daniel Wagner, "Evaluation of Young's Modulus of Polymers from Knoop Microindentation Tests," Polymer Communications, 1998, pp. 2387–2390, vol. 39, No. 11.

Shinozaki, D.M. and Y. Lu, "Micro–Indentation Relaxation Measurements in Polymer Thin Films," Journal of Electronic Materials, 1997, pp. 852–858, vol. 26, No. 7.

"Standard Test Method for Rubber Property–International Hardness," American Socity for Testing and Materials, pp. 1–4.

Wiergenga, P.E. and A.J.J. Franken, "Ultramicroindentation Apparatus for the Mechanical Characterization of Thin Films," J. Appl.Phys., Jun. 1984, pp. 4244–4247, 55 (12).

"Handle–O–Meter" Thwing–Albert Instrument Company, Philadelphia, PA.

Ali, S.I. and Shahida Begum, "Fabric Softeners and Softness Preception", Ergonomics, v.37, No. 5, pp. 801–806 (1994).

Grover, G. et al., "A Screening Technique for Fabric Handle", J. Text. Inst., 1993, 84 No. J. Textile Institute, pp. 486–494.

Kim, J.O. and B. Lewis Slaten, "Objective Assessment of Fabric Handle in Fabrics Treated With Flame Retardants," Journal of Testing and Evaluation, JTEVA, vol. 24, No. 4, Jul. 1996, pp. 223–228.

*Odian, Principles of Polymerization, 3rd Ed., John Wiley & Sons, Inc. (1991).

Osterberg, Peter M. and Stephen D. Senturia, "M–Test: A Test Chip for MEMS Material Property Measurement Using Electrostatically Actuated Test Structures,"0 Journal of Microelectromechanical Systmes, vol. 6, No. 2, Jun. 1997.

Pan, Ning and K.C. Yen, "Physical Interpretations of Curves Obtained Through the Fabric Extraction Process for Handle Measurement," Textile Research Journal 62(5), pp. 279–290 (1992).

Raeel, Mastura and Jiang Liu, "An Empirical Model for Fabric Hand" Textile Research Journal 62, 1, pp. 31–38 (1991).

*Timoshenko, S., Theory of Plates and Shells, McGraw–Hill, New York 1940.

Young, W.C., Roark's Formulas for Stress and Stain, 1989.

*U.S. Application No. 09/939,404 entitled "High Throughput Mechanical Property and Bulge Testing of Material Libraries," (D. Hajduk et al.) filed on Aug. 24, 2001.

*U.S. Application No. 09/939,252 entitled "High Throughput Mechanical Rapid Serial Property Testing of Material Libraries," (P. Mansky) filed on Aug. 24, 2001.

*U.S. Application No. 09/939,139 entitled "High Throughput Fabric Handle Screening," (M. Kossuth et al.) filed on Aug. 24, 2001.

*U.S. Application No. 09/939,149 entitled "High Throughput Rheological Testing Of Materials" (Paul Mansky et al.) filed on Aug. 24, 2001.

*U.S. Application No. 09/939,263 entitled "High Throughput Mechanical Property Testing of Materials Libraries Using Capacitance," (D. Hajduk et al.) filed on Aug. 24, 2001.

*U.S. Application No. 09/938,994 entitled "High Throughput Mechanical Property Testing of Materials Libraries Using a Piezoelectric," (D. Hajduk) filed on Aug. 24, 2001.

*The family of applications for U.S. Application No. 09/580,024 entitled "Instrument for High Throughput Measurement of Material Physical Properties and Method of Using Same," (Carlson, et al.) filed on May 26, 2000.

*The family of applications for U.S. Application No. 09/174,856 titled "Graphic Design of Combinatorial Material Libraries" (Lacy, et al.) filed on Oct. 19, 1998.

*U.S. Application No. 09/801,165 entitled "Method and Apparatus for Characterizing Materials By Using a Mechanical Resonator" filed Mar. 7, 2001.

*PCT Application No. PCT/US01/11417 entitled "Automated Process Control And Data Management System And Methods", filed Apr. 6, 2001.

*U.S. Application No. 09/420,334 entitled "Graphic Design of Combinatorial Material Libraries" (Lacy, et al.) filed on Oct. 18, 1999.

*U.S. Application No. 09/305,830 titled "Synthesizing Combinatorial Libraries of Materials" (Rust, et al.) filed on May 5, 1999.

*U.S. Application No. 09/550,549 entitled "Automated Process Control And Data Management System And Methods" (Crevier, et al.) filed on Apr. 14, 2000.

*U.S. Application No. 09/755,623 entitled "Laboratory Database System and Methods For Combinatorial Materials Research" (Dorsett, Jr., et al.) filed on Jan. 5, 2001.

*The family of applications for U.S. Application No. 09/227,558 entitled, "Apparatus and Method of Research for Creating and Testing Novel Catalysts, Reactions and Polymers" (Turner et al.) filed Jan. 8, 1999.

*The family of applications for U.S. Application No. 09/211,982 entitled "Parallel Reactor With Internal Sensing" (Turner et al.) filed Dec. 14, 1998.

*U.S. Application No. 09/235,368 entitled "Polymerization Method From the Combinatorial Synthesis and Analysis of Organometallic Compounds and Catalysts" (Weinberg et al.) filed on Jan. 21, 1999.

*U.S. Application No. 60/122,704 entitled "Controlled, Stable Free Radical Emulsion and Water–Based Polymerizations" (Klaerner et al.) filed on Mar. 9, 1999.

*The family of applications for U.S. Applicaiton No. 09/156,827 entitled "Formation of Combinatorial Arrays of Materials Using Solution–Based Methodologies" (Giaquinta et al.) filed Sep. 18, 1998.

*The family of applications for U.S. Application No. 09/567,598 entitled "Polymer Libraries on a Substrate, Method for Forming Polymer Libraries on a Substrate and Characterization Methods with Same" (Boussie et al.) filed May 10, 2000.

*U.S. Application No. 09/579,338 entitled "Rheo–Optical Indexer and Method of Screening and Characterizing Arrays of Materials" (Carlson et al.) filed on May 25, 2000.

* cited by examiner

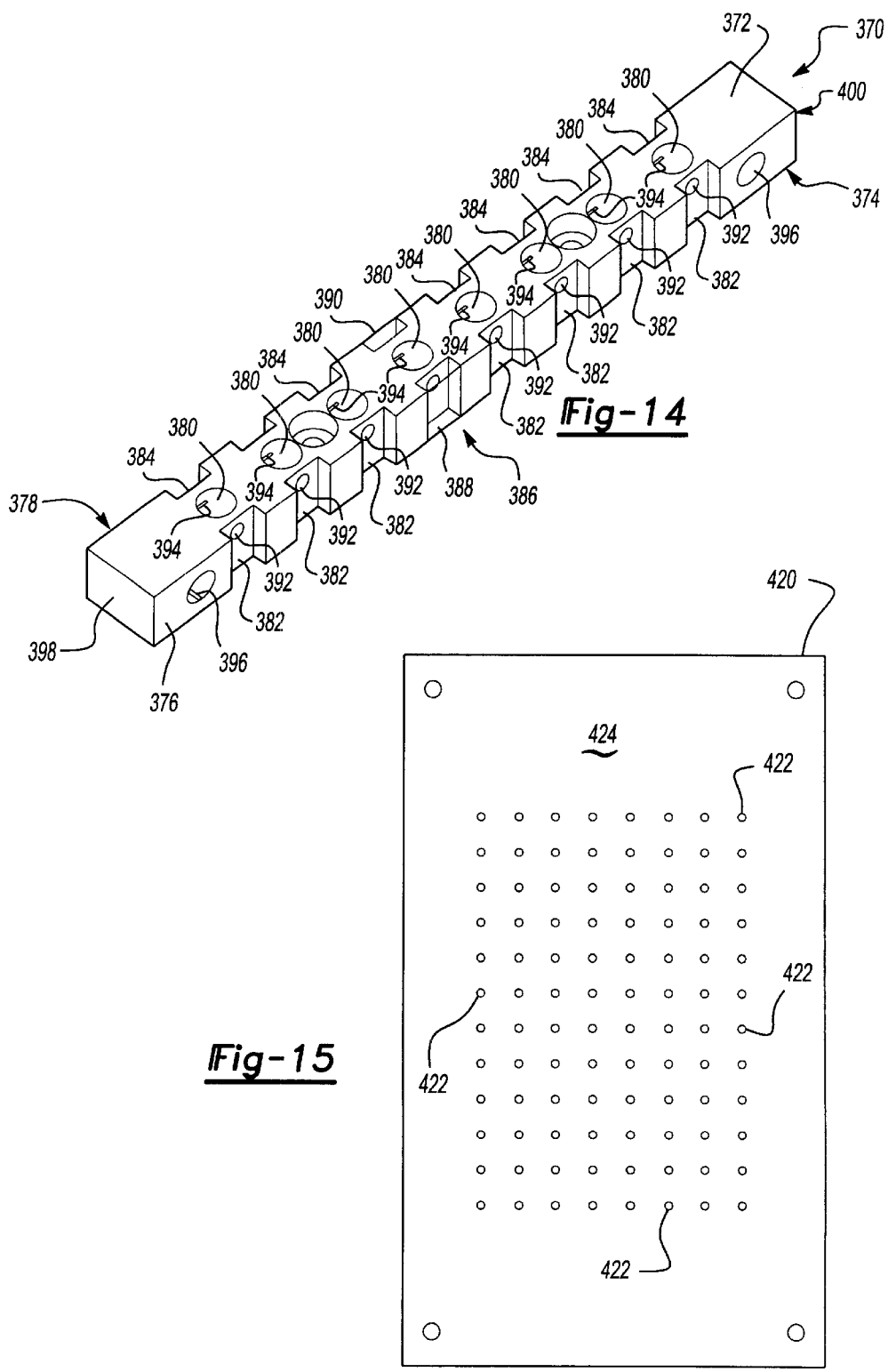

HIGH THROUGHPUT VISCOMETER AND METHOD OF USING SAME

BACKGROUND

1. Technical Field

The present invention relates to a device and technique for measuring viscosity and related properties of multiple samples, in some embodiments simultaneously, and is particularly useful for rapidly screening and characterizing a combinatorial library of materials.

2. Discussion

Combinatorial chemistry generally refers to methods and materials for creating collections of diverse materials or compounds—commonly known as libraries—and to techniques and instruments for evaluating or screening libraries for desirable properties. Combinatorial chemistry has revolutionized the process of drug discovery, and has enabled researchers to rapidly discover and optimize useful materials.

One useful screening criterion is viscosity, $\eta$, which is a physical property that characterizes a fluid's resistance to flow. For laminar flow of Newtonian fluids, including gases and simple liquids, viscosity is proportional to the tangential component of stress (shear force) divided by the local velocity gradient. Although complex fluids such as pastes, slurries, and high polymers do not follow the simple relationship between tangential stress and local velocity gradient, viscosity and its analogs nevertheless can serve as useful screening criteria. For example, one can use viscosity measurements to estimate molecular weights of polymers in solution.

Combinatorial libraries routinely comprise hundreds or thousands of individual library members. As a result, most viscometers are unsuitable for screening purposes because they were designed to slowly process one sample at a time. Although generally the throughput of serial instruments and techniques can benefit from automation, many viscometers have relatively long response times, require time-consuming sample preparation, and exhibit sluggish temperature control, making such instruments impractical for use as screening tools.

The present invention overcomes, or at least mitigates, some or all the problems discussed above.

SUMMARY OF THE INVENTION

The present invention provides an apparatus for measuring viscosity or related properties of fluid samples in parallel. In some embodiments, the apparatus includes a plurality of tubes and reservoirs in fluid communication with the tubes. Each of the tubes has a predetermined length and a uniform inner diameter over at least a portion of the tube's length. In addition, the tubes provide flow paths for the fluid samples, which are initially contained within the reservoirs. The apparatus also includes a mechanism for filling the reservoirs with the fluid samples, and a device for determining volumetric flow rates of fluid samples flowing from the reservoirs through the plurality of tubes simultaneously. The disclosed apparatus is capable of measuring viscosity or related properties of at least five fluid samples simultaneously.

The present invention also provides an apparatus comprised of an array of syringes for measuring viscosity or related properties of fluid samples in parallel. Each of the syringes includes a barrel for containing the fluid samples, a plunger located within the barrel for aspirating the fluid samples into the barrel, and a hypodermic needle in fluid communication with the barrel. The hypodermic needle, which has a substantially uniform diameter over a majority of its length, provides a flow path for the fluid samples. The apparatus also includes upstream and downstream detector arrays that are located along the barrel of each syringe. The detector arrays, which monitor volumetric flow rates of the fluid samples through each hypodermic needle, are capable of measuring viscosity or related properties of at least five fluid samples simultaneously.

Additionally, the present invention includes a method of screening fluid samples. The method comprises (1) providing fluid samples to a plurality of reservoirs; (2) allowing the fluid samples to flow from the reservoirs through a plurality of tubes; and (3) detecting the volumetric flow rates of at least five of the fluid samples through each of the tubes simultaneously.

Another embodiment of the present invention uses the same viscometer design with upstream and downstream detectors described above, but places at least one of those viscometers on tip of the arm of a three axis robot, and preferably at least two viscometers are placed on the tip of at least two arms of a three axis robot. In this embodiment, the viscometer is operated in the same manner described above and is moved from well to well of a sample tray or combinatorial library of samples. Many known liquid handling systems incorporate one or more tips and the viscometer may be placed on as many tips as are present in the robot being used. In addition, when multiple arm robots with multiple tips are used a high throughput instrument for viscosity measurements is provided. For example 8 tips on a 9 mm pitch may be provided on one or more arms of the robot. Thus, this embodiment of the present invention is either a rapid serial measurement or a simultaneous measurement on multiple samples.

BRIEF DESCRIPTION OF THE DRAWINGS

FIG. 14 shows a perspective view of a detector block module.

FIG. 15 shows a top view of an optional needle alignment block.

DETAILED DESCRIPTION OF THE PREFERRED EMBODIMENTS

Overview of Parallel Viscometer

A parallel viscometer made in accordance with the present invention generally includes two or more tubes. The tubes can be constructed of any material, but stainless steel is particularly useful because of its mechanical strength, high thermal conductivity, and excellent dimensional stability and control. Each of the tubes has a substantially uniform inner diameter, d, over at least a portion of its length, l, which defines a viscosity measurement region. Typically, this region is the same for each of the tubes and coincides with their total lengths, but one can vary the inner diameter and length of individual tubes to account for differences in sample viscosity. In addition, the inner diameter of the tubes may assume any value as long as the Reynolds Number, R, which provides a measure of inertial forces to viscous forces within a liquid sample is less than about $10^3$—i.e., liquid flow within the tubes is laminar. From a practical standpoint, d and l are usually minimized to allow viscosity measurements using as little of the samples as possible. This is often the case when screening combinatorial libraries because the amount of any particular sample or library member can be as small as about $10^2$ $\mu l$.

The parallel viscometer also includes reservoirs for holding the liquid samples prior to their introduction in the tubes. The reservoirs should be chemically inert, and therefore suitable fabrication materials include glass, PTFE, aluminum, and stainless steel. As noted below, it is often desirable to monitor the volumetric flow rate through the tubes by detecting changes in sample volume within the reservoir. Since optical techniques are well suited for this task, the reservoirs are often made of a transparent material such as glass. The reservoir may be above or below the tube.

Figure 1:
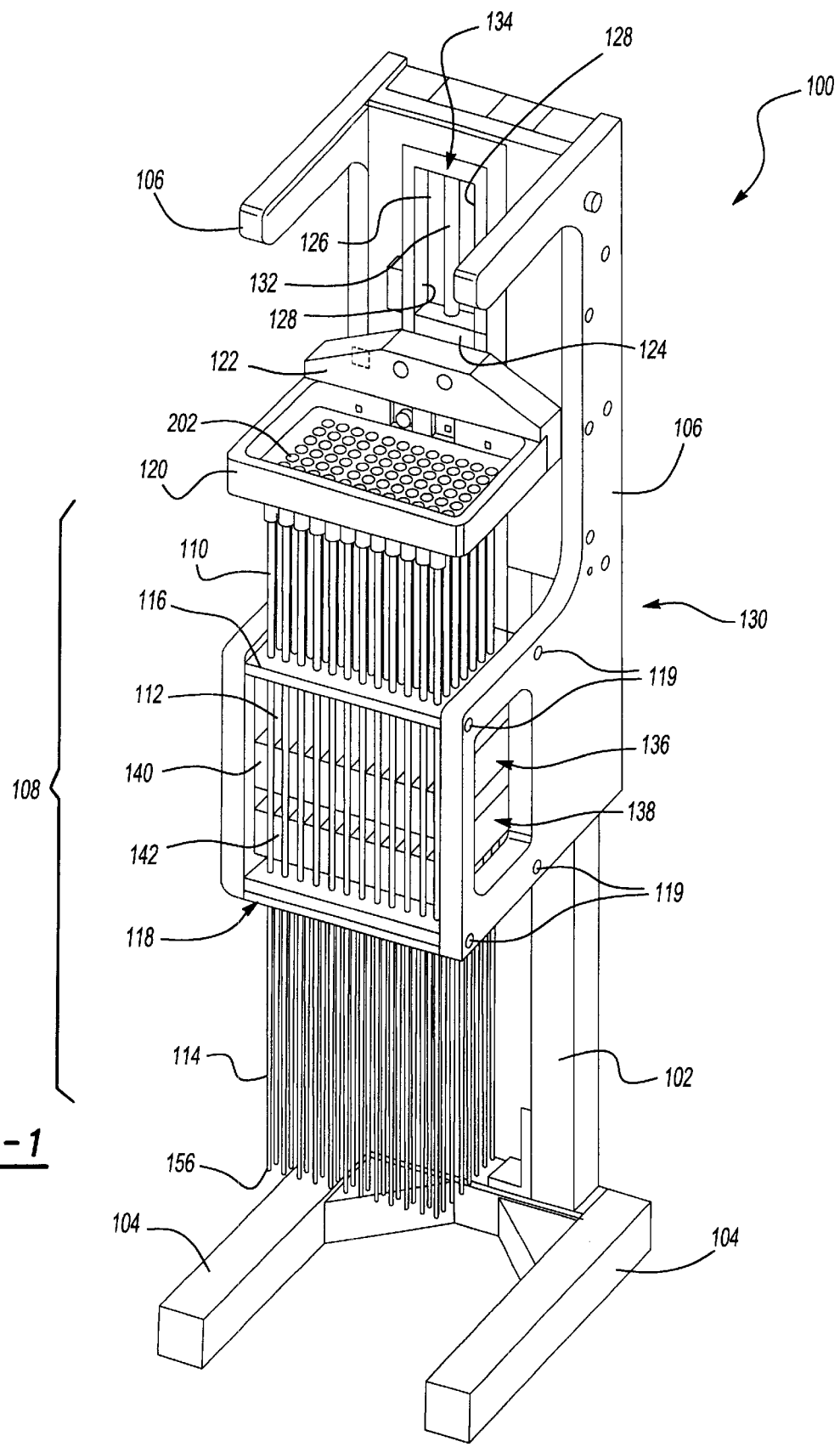
FIG. 1 is a perspective front view of a parallel viscometer.

In addition, the parallel viscometer includes a mechanism for filling the reservoirs with the samples. Suitable filling mechanisms include aspiration via fluid connection to a vacuum source; manual or automatic transfer of liquid samples using a single-channel or multiple-channel pipette; and direct loading and subsequent melting of solid samples. As illustrated in FIG. 1, syringe needles and barrels can serve as the viscosity measurement regions (tubes) and the reservoirs, respectively. When using syringes, the reservoirs (barrels) can be aspirated by withdrawal of the syringe plungers.

Generally, the parallel viscometer also includes a device for monitoring the volumetric flow rate, Q, of the samples flowing through the tubes. As described below, once the volumetric flow rate is known, one may calculate the viscosity of the samples from the Hagen-Poiseulle equation, which relates fluid viscosity to the volumetric flow rate and the pressure drop, $\Delta P$, across the viscosity measurement region of an individual tube. For gravity-driven flows, the pressure drop comprises the product of the sample density, the gravitational acceleration, and the length of the viscosity measurement region. When gravity is insufficient to induce flow—i.e., when sample viscosity or capillary forces are large—the parallel viscometer includes a mechanism for applying and monitoring a force (pressure) that drives the liquid samples through the tubes. Typically, the parallel viscometer employs rams or pistons within the reservoirs to drive the fluid samples through the tubes.

Useful devices for monitoring the volumetric flow rate include sensor pairs located at upstream and downstream positions along each of the reservoirs. Each sensor may comprise a light source and a light detector, which generates a signal in response to a momentary interruption of light resulting from a passing liquid meniscus, a change in liquid opacity, or a shift in refractive index. Alternatively, each sensor may consist of a heated wire that generates a signal in response to a change in electrical resistance resulting from dissimilarities in heat transfer characteristics of liquids and gases. Other useful detector pairs include magnetic sensors that generate a signal in response to movement of a magnet float within the sample fluid, and conductivity sensors that respond to differences in electrical conductivity among fluids. In any case, the two signals from the sensor pairs delimit the time interval for a known volume of sample to pass through the viscosity measurement region (tube), which allows calculation of Q.

Other techniques and devices for measuring or inferring Q include measuring the mass of discrete samples that exit the tubes during a predetermined time interval, and monitoring changes in electrical capacitance of an electrically conductive cylindrical reservoir and coaxial wire. In the latter technique, the capacitance of the system varies as the ratio of liquid sample to air in the reservoir changes. The parallel viscometer may also employ proximity sensors to measure the speed of rams or pistons when screening high viscosity samples. Regardless of the detection system employed, the parallel viscometer typically uses an A/D data acquisition board in tandem with a computer and necessary software to record sensor output and to determine Q.

The parallel viscometer also includes one or more receptacles for collecting samples exiting the tubes. Since the samples are often reused in subsequent screening experiments, the tubes are typically supplied with separate receptacles to prevent cross-contamination of samples. Useful receptacles include wells of standard ninety-six well microtiter plates. Because viscosity is a strong function of temperature, the parallel viscometer may optionally include an environmental chamber for maintaining the fluid samples at a constant temperature.

Overview of the Viscometer on a Robotic Arm Tip

In this embodiment of the present invention, a three-axis robot is provided having at least one arm and at least one tip on that at least one arm. A single viscometer as described above is placed on a tip of the arm of the robot. For example, a syringe may be fitted over the robotic tip with a vacuum tight seal, effectively becoming part of the tip. The needle can be inserted into one of the sample wells (e.g. in a 96 well plate) and liquid aspirated into the barrel or tube by reducing the pressure in the barrel or tube. This may be done either by retracting the plunger on a separate syringe pump, such as provided to aspirate and dispense liquids in an automated liquid handling system, or by shunting the line to a vacuum source. Once a sufficient quantity of liquid is aspirated into the barrel, the syringe is lifted above the sample's liquid level, and the liquid is allowed or forced to flow through the needle and back into the sample well from which it was drawn. The flow may be monitored by any of a variety of mechanisms described herein. When the measurement is complete, the syringe can be cleaned automatically in a number of ways prior to making the next measurement. Three axis robots are well known in the art and are commercially available, such as those available from Cavro Scientific Instruments (Sunnyvale, Calif.); see also U.S. Pat.

Nos. 5,476,358 and 5,324,163 and WO 99/51980, which are all incorporated herein by reference. In addition, the number of viscometers is dependent on the number of tips present in the chosen robot. If a multi-arm, multi-tipped robot is chosen, then 2, 4, 8, 16 or more viscometers can take measurements in accord with the disclosure herein simultaneously or in rapid serial mode.

Throughout and in accord with this specification, the number of viscometers is a methodology and design choice those of skill in the art can make in view of this specification. A ninety-six parallel viscometer is detailed below, however, lower or higher throughput requirements may serve the needs of a particular application of this invention and thus, 8 or more, 16 or more, 24 or more or 48 or more viscometers in parallel are within the scope of this invention. Generally, an array of materials comprises a plurality of materials for which a viscosity measurement is a desired measurement. In other embodiments, an array of materials will comprise 8 or more, 16 or more, 24 or more or 48 or more materials, each of which is different from the others. Arrays and methods of making such arrays are described in detail, for example, U.S. Pat. No. 6,004,617 and U.S. patent application Ser. No. 09/227,558, filed Jan. 8, 1999, both of which are incorporated herein by reference for all purposes.

Ninety-Six Element Parallel Viscometer

FIG. 1 shows a perspective front view of a parallel viscometer 100 that can measure viscosity of ninety-six samples simultaneously. The viscometer 100 includes a rigid frame 102 mounted on a supporting base 104. A pair of side plates 106, which are attached to the rigid frame 102, support a set of syringes 108 that serve as the reservoirs and tubes described in the overview section. The viscometer 100 shown in FIG. 1 has ninety-six syringes 108 or measuring elements, although the number of syringes 108 used can vary. Each of the syringes 108 includes a plunger 110, a barrel 112, and a hollow elongated needle or capillary tube 114. As described below, a barrel retaining plate 116 and a needle capture assembly 118 hold each syringes 108 in place. The barrel retaining plate 116 and the needle capture assembly 118 are securely fastened to the side plates 106 using threaded fasteners 119, which prevent movement of each syringe barrel 112 and capillary tube 114 during viscosity measurement.

As noted in FIG. 1, the parallel viscometer 100 also includes a plunger plate 120 that provides uniform translation of each plunger 110 in a direction parallel to its longitudinal axis. A mounting bracket 122 connects the plunger plate 120 to a translation block 124 located within a guide channel 126. The guide channel 126 is attached to the rigid frame 102 and has a pair of planar side walls 128 that are substantially parallel to the travel direction of each plunger 110. The small clearance between the guide channel 126 side walls 128 and the translation block 124 allow the block 124 to slide freely within the guide channel 126 with minimal lateral motion. In this way, the translation block 124 and the guide channel 126 restrict the movement of the plunger plate 120 to a direction substantially parallel to the longitudinal axis of each plunger 110.

A DC motor (not shown), which is mounted on the rigid frame 102 between the set of syringes 108 and the back plane 130 of the viscometer 100, drives the plunger plate 120. The translation block 124, which is connected to the plunger plate 120, is fastened to a threaded rod or drive shaft 132, which is located within the guide channel 126. The drive shaft 132 is mechanically connected to the motor using appropriate gearing and extends from the motor to one end 134 of the guide channel 126. Because the drive shaft is stationary, the translation block 124 and the plunger plate 120 move away or toward each syringe barrel 112 when the motor rotates the drive shaft 132. The translation direction of the plunger plate 120 depends on the rotation direction of the drive shaft 132. Typically, a microprocessor-based motor controller (not shown) regulates the speed and direction of the motor and hence the translation speed and direction of the plunger plate 120.

The parallel viscometer 100 also includes an upstream detector array 136 and a downstream detector array 138, which monitor the volumetric flow rate, Q, of the samples flowing through each syringe barrel 112 and capillary tube 114. The detector arrays 136, 138 are made up of twelve linear arrays 140, 142, each having eight elements (not shown) spaced nine millimeters apart. The resulting twelve-by-eight or ninety-six-element detector arrays 136, 138 allow the set of syringes 108 to have the same lateral spacing as a standard ninety-six well microtiter plate. Each of the detector elements is comprised of an infrared source such as an IR LED, and an infrared detector, which are aligned on opposing sides of each syringe barrel 112. As described below, for each of the syringes 108, the upstream 136 and downstream 138 detector arrays monitor Q by noting the time it takes for a liquid meniscus within the syringe barrel 112 to travel between the upstream detector element and the downstream detector element.

Figure 2:
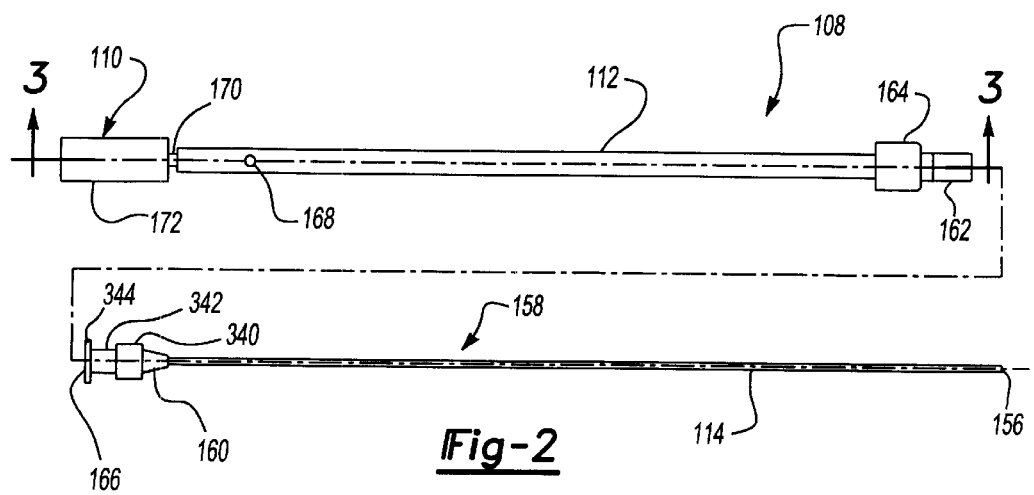
FIG. 2 shows a partial exploded view of one of the syringes that comprises the parallel viscometer.

FIG. 2 shows a partial exploded view of one of the syringes 108. The syringe 108 includes a flat-tipped 156 stainless steel hypodermic needle 158 having a capillary tube 114 portion that serves as the viscosity measurement region. Although each capillary tube 114 shown in FIG. 1 has the same dimensions, the length and inner diameter of each capillary tube 114 can vary to accommodate samples possessing a broad range of viscosities. One end of the capillary tube 114 has a standard Luer hub 160, which is used to connect the capillary tube 114 to the syringe barrel 112. The capillary tube 114 shown in FIG. 2 has a six-inch length and a 0.040-inch inner diameter, though generally, the length and the inner diameter of the capillary tube 114 is chosen to achieve a reasonable viscosity measurement time. Typical measurement times are from about ten seconds to about one minute.

Each syringe barrel 112 functions as a reservoir for a particular measuring element of the parallel viscometer 100. The syringe barrel 112 depicted in FIG. 2 is fabricated from glass and has a cylindrical bore (not shown) extending throughout its length. A PTFE Luer tip 162 is attached to one end of the syringe barrel 112 using a stainless steel end cap 164. The Luer tip 162 has the shape of a truncated cone that mates with a slightly tapered, cylindrical internal cavity 166 of the Luer hub 160. During assembly of each of the syringes 108, the Luer tip 162 is press-fit into the Luer hub 160 to create a gas-tight seal between the capillary tube 114 and the syringe barrel 112. The syringe barrel 112 shown in FIG. 2 has a five-inch length and a 0.2-inch internal diameter, providing a maximum reservoir volume of about 250 $\mu$l. The syringe barrel 112 also has a 0.04-inch diameter vent hole 168 bored through its wall, which allows fluid communication with the cylindrical bore of the syringe barrel 112 and the environment. The dimensions of the syringe barrel 112, as well as the size and the location of the vent hole 168 can vary among syringes 108.

As noted in FIG. 2, each of the syringes 108 also includes a plunger 110, which can be used to aspirate a liquid sample into particular syringes 108 or to drive the sample through the capillary tube 114. The plunger 110 includes a rigid cylindrical rod 170 and a plunger button 172 that delimits a portion of the plunger 110 located outside the syringe barrel 112. As described below, the plunger button 172 connects the plunger rod 170 to the plunger plate 126 shown in FIG. 1.

Figure 3:
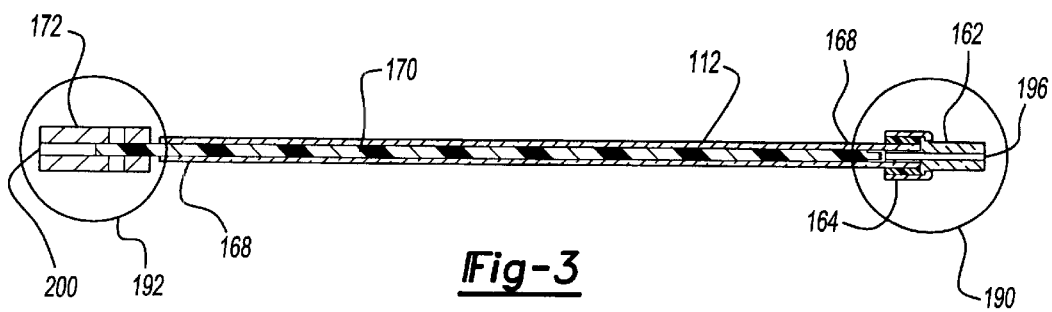
FIG. 3 shows a cross sectional view of a syringe barrel and plunger.
Figure 4:
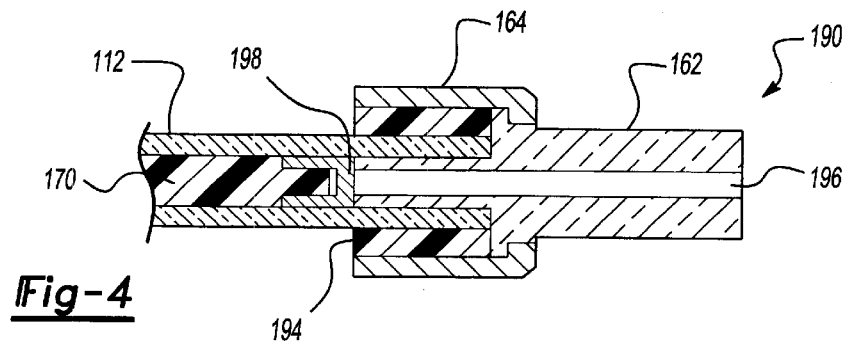
FIG. 4 shows a close-up, cross-sectional view of a first end of a syringe barrel.
Figure 5:
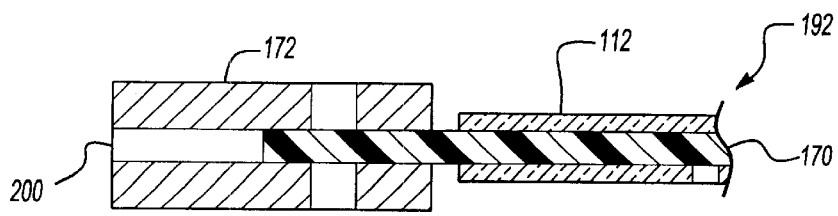
FIG. 5 shows a close-up, cross-sectional view of a second end of a syringe barrel.

FIGS. 3, 4 and 5 provide further details of the syringes 108. FIG. 3 shows a cross-sectional view of the syringe barrel 112 and the plunger 110; FIG. 4 and FIG. 5 show, respectively, close-up cross-sectional views of first 190 and second 192 ends of the syringe barrel 112. As noted above, the syringe barrel 112 has a Luer tip 162 that is attached to the first end 190 of the syringe barrel 112 using an end cap 164. A deformable sleeve 194 is placed between the end cap 164 and the syringe barrel 112 to provide a gas-tight seal between the end cap 164, the Luer tip 162, and the syringe barrel 112. The Luer tip 162 has a 0.04-inch cylindrical through-hole 196 extending along its longitudinal axis, which provides fluid communication between the cylindrical bore of the syringe barrel 112 and the interior of the capillary tube 114. The dimensions of the through-hole 196 can vary among syringes 108.

As shown in FIG. 3 and FIG. 4, the portion of the plunger 110 within the first end 190 of the syringe barrel 112 includes a resilient plunger tip 198 attached to the plunger rod 170. The plunger tip 198 has a cylindrical outer surface with a nominal outer diameter slightly larger than the internal diameter of the syringe barrel 112. In the embodiment shown in FIG. 3 and FIG. 4, the plunger tip 198 compresses when placed within the syringe barrel 112, providing a gas-tight seal between the cylindrical bore of the syringe barrel 112 and the plunger tip 198, though a gas-tight seal is sometimes unnecessary. Ordinarily, the plunger tip 198 should be more compressible than the syringe barrel 112 and should be made of a chemically inert material such as PTFE. The portion of the plunger 110 located adjacent the second end 192 of the syringe barrel 112, includes a plunger button 172 attached to the plunger rod 170. The plunger button 172 includes a threaded hole 200 that allows attachment of the plunger 110 to the plunger plate 120 (FIG. 1) using threaded fasteners 202.

Figure 6:
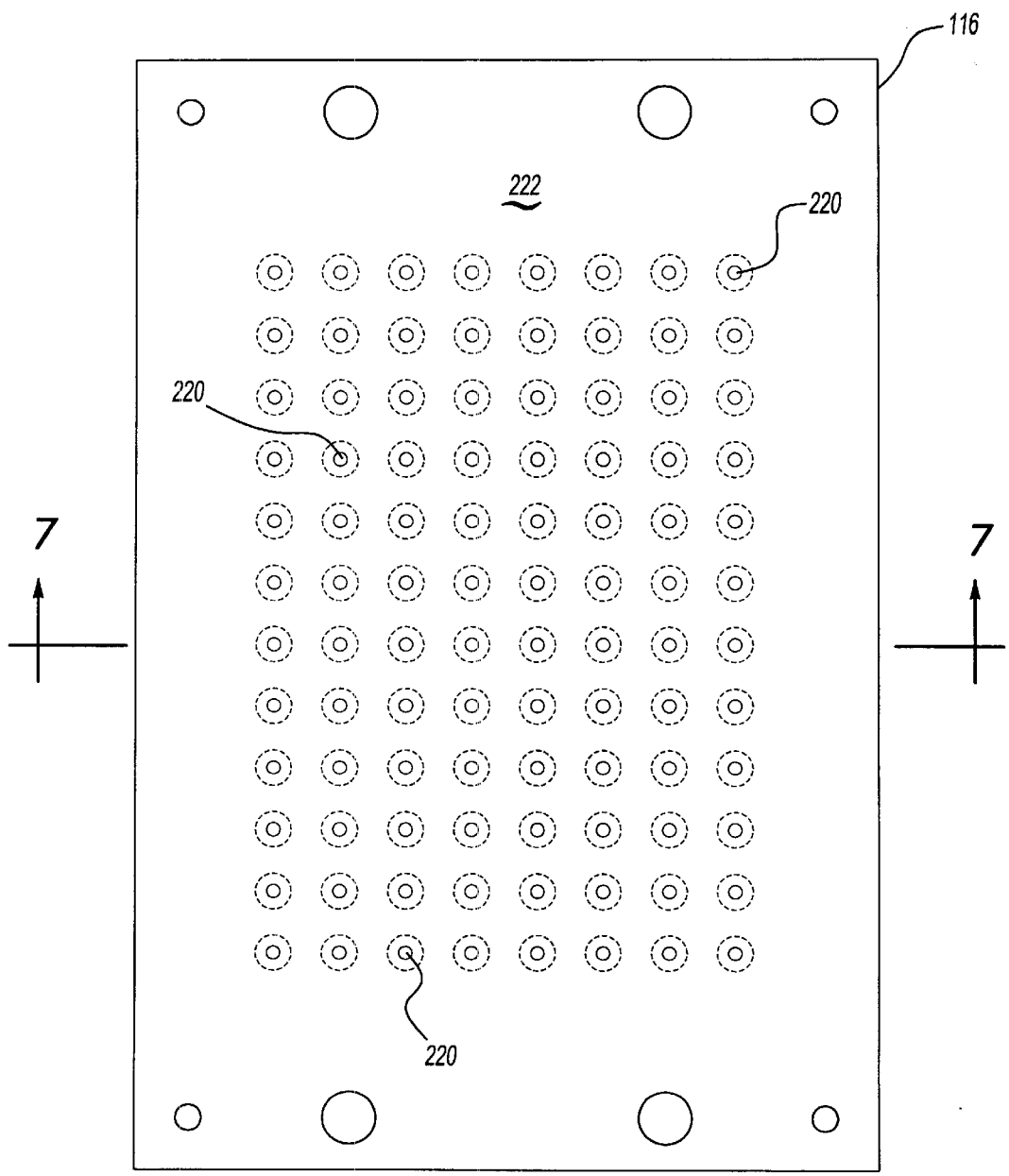
FIG. 6 shows a top view of a barrel retaining plate.
Figure 7:
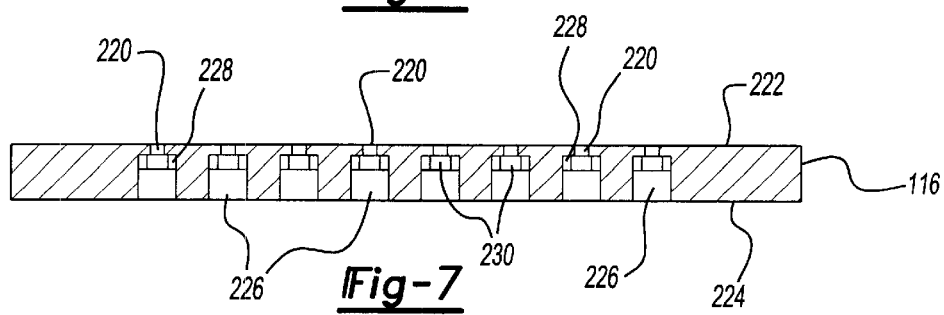
FIG. 7 shows a cross sectional view of a barrel retaining plate.

FIG. 6 and FIG. 7 show a top view and a cross sectional view, respectively, of the barrel retaining plate 116. As noted in the discussion of FIG. 1, the barrel retaining plate 116 and the needle capture assembly 118, help secure each of the syringes 108 during viscosity measurement. The barrel retaining plate 116 is ordinarily fabricated from a rigid material such as aluminum, and includes a plurality of plunger through-holes 220 that extend from an upper surface 222 of the plate 116 to a lower surface 224 of the plate 116. Like the well spacing of a standard ninety-six well microtiter plate, the through-holes 220 shown in FIG. 6 are arrayed on nine-mm centers. As shown in FIG. 7, the through-holes 220 allow passage of syringe plunger rods 170, but prevent movement of syringe barrels 112 through the upper surface 222 of the barrel retaining plate 116. The through-holes 220 include counter bores 226 that extend from the lower surface 224 of the plate 116 partially into the barrel retaining plate 116. The size of each of the counter bores 226 is sufficient to receive a second end 192 (FIG. 3) of each of the syringe barrels 112. The barrel retaining plate 116 typically includes resilient washers 228 that sit within the counter bores 226 and cushion the syringe barrels 112 during assembly and operation of the viscometer 100. Each of the washers 228 has an internal bore 230 at least as large as the through-holes 220 to allow movement of the plunger rods 170.

Figure 8:
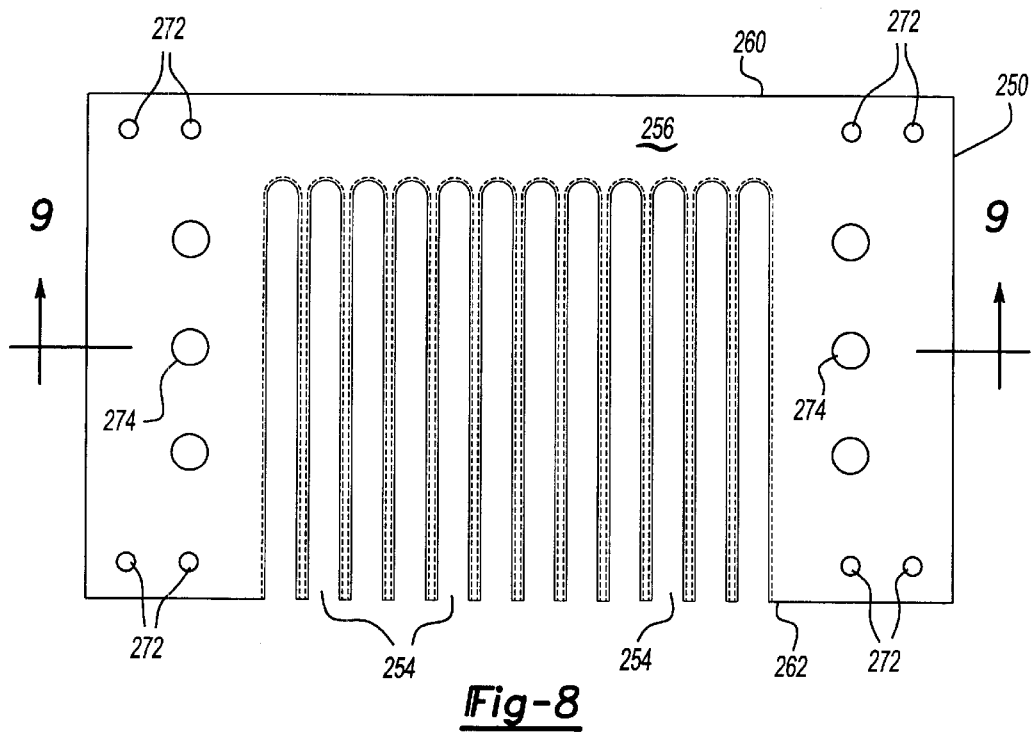
FIG. 8 shows a top view of a Luer hub capture plate.
Figure 9:
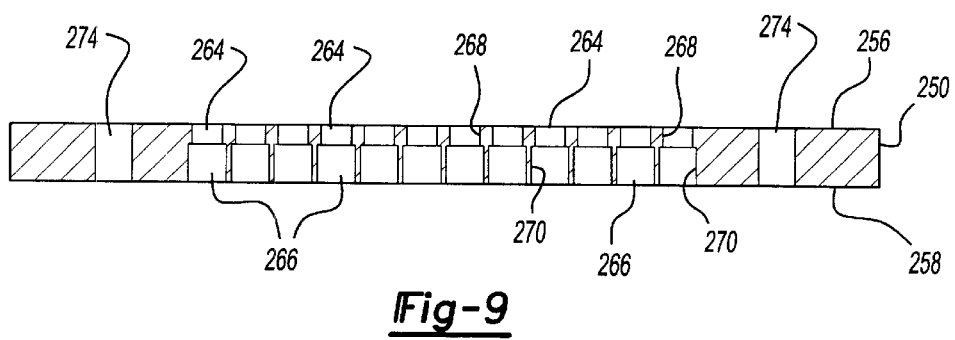
FIG. 9 shows a cross sectional view of a Luer hub capture plate.

FIG. 8–FIG. 11 provide details of the needle capture assembly 118, which comprises a Luer hub capture plate 250 and a needle preload block 252. FIG. 8 and FIG. 9 show, respectively, top and cross sectional views of the Luer hub capture plate 250, which is typically fabricated from a rigid material such as aluminum. The Luer hub capture plate 250 includes a set of channels 254 that extend from an upper surface 256 to a lower surface 258 of the plate 250, and from a region adjacent a front edge 260 of the plate 250 to a back edge 262 of the plate 250. Each of the channels 254 comprises an upper channel portion 264 and a lower channel portion 266 that are located adjacent the upper and lower surfaces 256, 258 of the plate 250. The upper and lower channel portions 264, 266 have generally parallel and planar side walls 268, 270 that define uniform channel widths. As shown in FIG. 9, the width of the upper channel portion 264 is greater than the width of the lower channel portion 266. The Luer hub capture plate 250 includes a first group of through-holes 272 for aligning the capture plate 250 and the preload block 252, and a second group of through-holes 274 (threaded) for attaching the capture plate 250 to the preload block 252.

Figure 10:
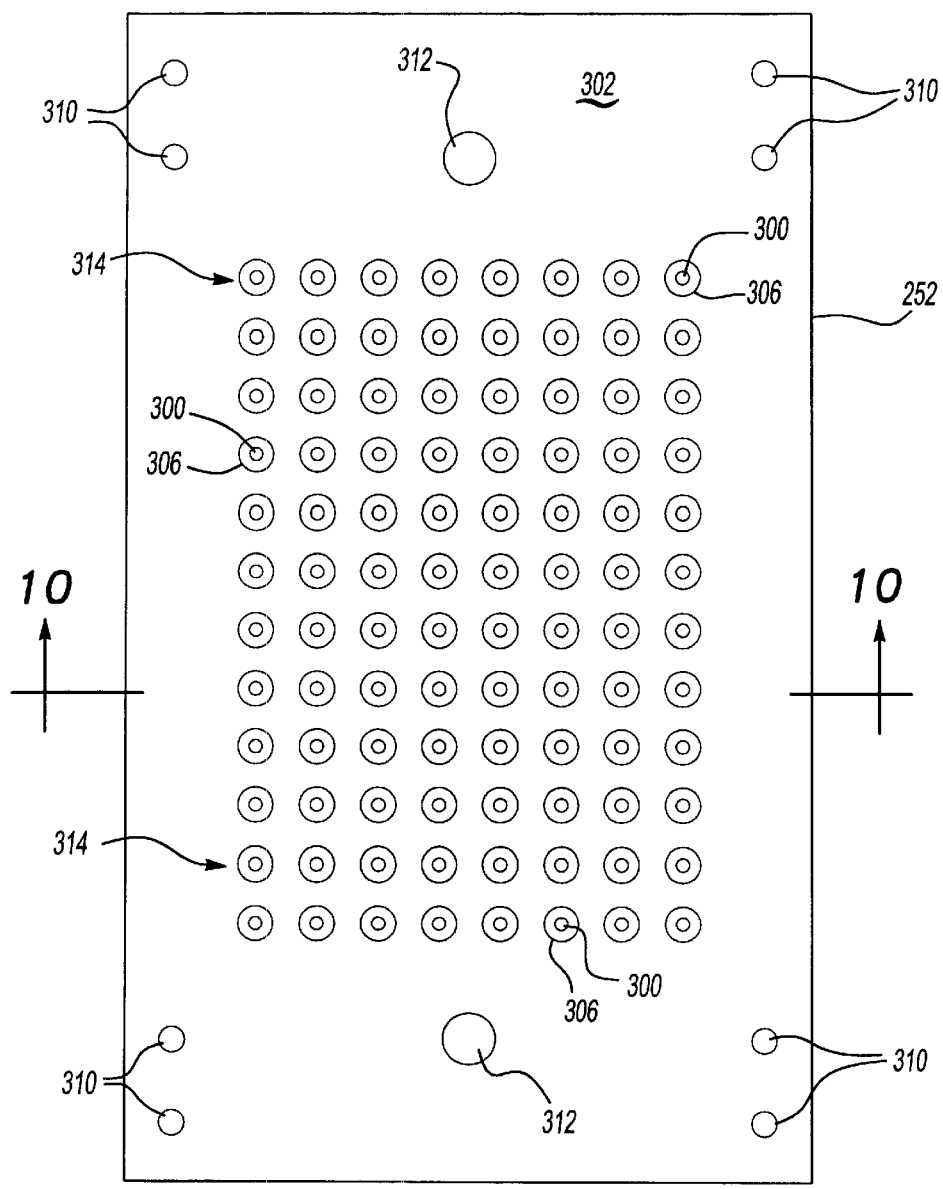
FIG. 10 shows a top view of a preload block.
Figure 11:
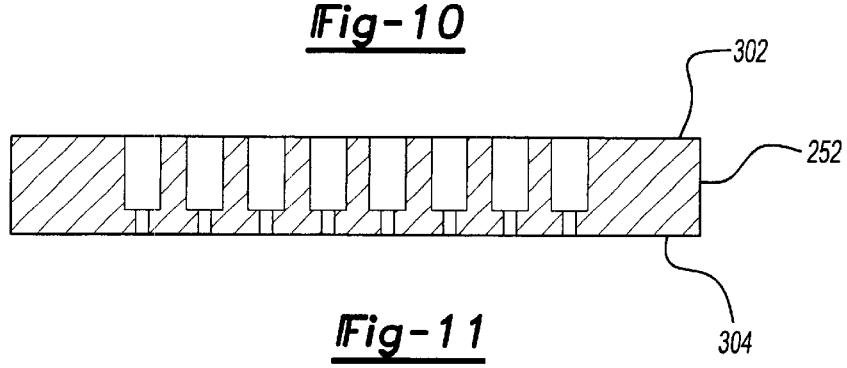
FIG. 11 shows a cross sectional view of a preload block.

FIG. 10 and FIG. 11 show top and cross sectional views, respectively, of the preload block 252. The preload block 252, like the Luer hub capture plate 250, is typically fabricated from a rigid material such as aluminum. The preload block 252 includes through-holes 300 that extend from an upper surface 302 of the block 252 to a lower surface 304 of the block 252. The through-holes 300 are arrayed on nine-mm center—corresponding to the well spacing of a standard ninety-six well microtiter plate—and include counter bores 306 that extend from the upper surface 302 part way into the preload block 252. The preload block 252 includes a second group of through-holes 310 for aligning the preload block 252 and the Luer-hub capture plate 250, and a third group of through-holes 312 for attaching the preload block 252 to the Luer hub capture plate 250.

Figure 12:
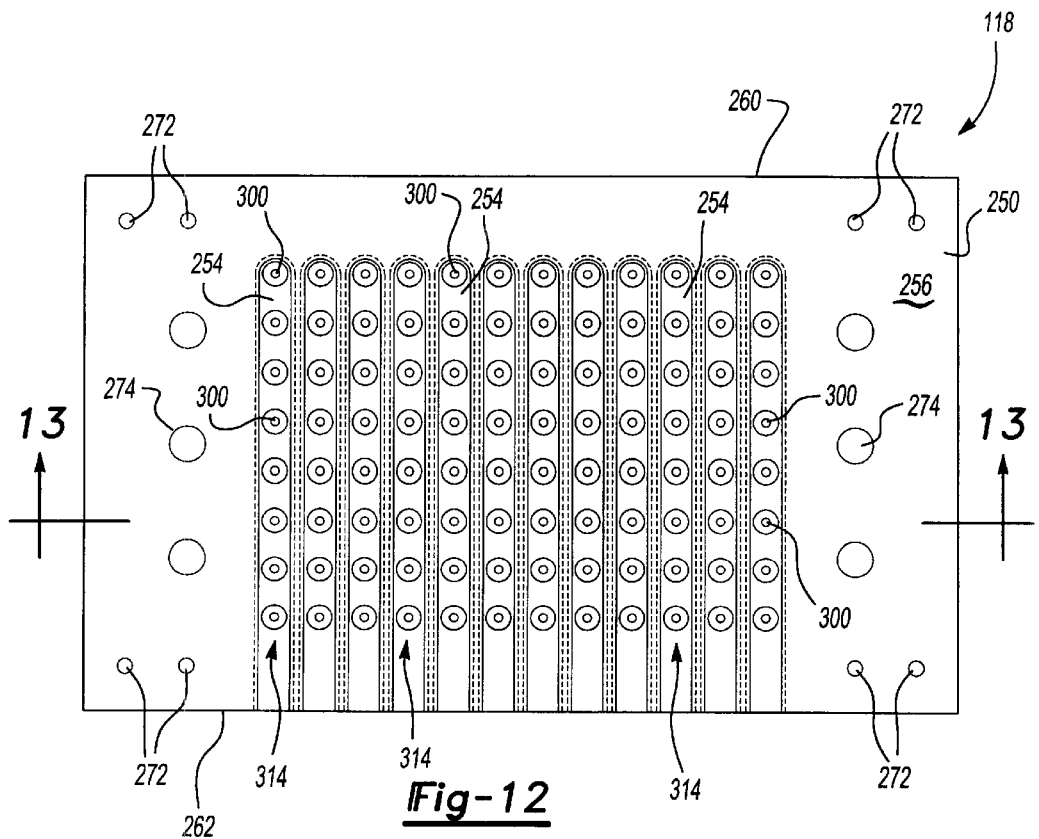
FIG. 12 shows a top view of a needle capture assembly.
Figure 13:
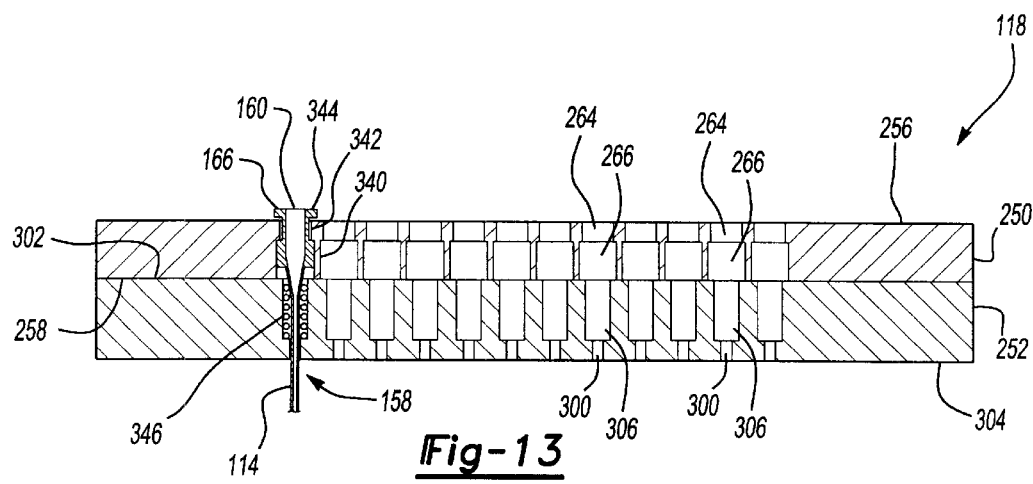
FIG. 13 shows a cross sectional view of a needle capture assembly.

FIG. 12 and FIG. 13 show, respectively, top and cross sectional views of the needle capture assembly 118, which is comprised of the Luer hub capture plate 250 and the needle preload block 252. The Luer hub capture plate 250 is disposed above (or on) the needle preload block 252 such that the first and second through-holes 272, 274 of the capture plate 250 line up, respectively, with the second and third through-holes 310, 312 of the preload block 252. Furthermore, each row 314 of through-holes 300 lines on the preload block 252 line up with one of the channels 254 of the capture plate 250. Since each channel 254 and row 314 can accommodate eight Luer hubs 160, and since the capture plate 250 and the preload block 252 have twelve channels 254 and twelve rows 314, respectively, the needle capture assembly 118 can secure up to ninety-six syringes 108 (FIG. 2).

FIG. 13 shows how the Luer hub capture plate 250 and the needle preload block 252 cooperate to secure a set of syringes 108 (FIG. 2). For clarity, the needle capture assembly 118 shown in FIG. 13 includes a single hypodermic needle 158, though typically each through-hole 300 of the needle preload block will contain a hypodermic 158 needle. The hypodermic needle 158 includes a capillary tube 114, which serves as a viscosity measurement region, and a Luer hub 160, which connects the capillary tube 114 to a syringe barrel 112. As noted in the description of FIG. 2, the Luer hub 160 has a tapered internal cavity 166 that can receive the conical-shaped Luer tip 162 of the syringe barrel 112. The Luer hub 160 also includes generally cylindrical body 340, neck 342 and flanged head 344 portions that in FIG. 13 are located, respectively, within the lower 266 and upper 264 channel portions and adjacent the upper surface 256 of the Luer hub capture plate 250. Since the diameters of the body 340 and flanged head 344 portions of the Luer hub 160 are larger than the width of the upper portions 264 of the channels 254, the Luer hub capture plate 250 limits axial translation of the hypodermic needle 158. In addition, each of the counter bores 306 in the needle preload block 252 typically receives a spring 346 that applies a force against the Luer hub 160 to resist axial movement of the hypodermic needles 158 and syringes 108.

Many methods can be used to load and assemble the needle capture assembly 118. For example, one method includes placing springs 346 in the counter bores 306 of the needle preload block 252 and inserting the capillary tube portion 114 of the hypodermic needles 158 through the springs 346, counter bores 306 and through-bores 300 of the preload block 252. Once the desired fraction of through-holes 300 contain hypodermic needles 158, the method calls for aligning the body 340 and neck 342 portions of the Luer hubs 160 with, respectively, the lower 266 and upper 264 channel portions along the back edge 262 of the Luer hub capture plate 250. The method includes sliding the Luer hubs 160 into the channels by translating the needle preload block 252 from the back edge 262 to the front edge 260 of the Luer hub capture plate 250. The process continues until the first and second through-holes 272, 274 of the capture plate 250 line up, respectively, with the second and third through-holes 310, 312 of the preload block 252. After alignment, the method concludes by attaching the preload-block 252 to the Luer hub capture plate 250 by twisting fasteners into the third 312 and second 272 through-holes of the needle preload block 252 and the Luer hub capture plate 250. After loading the hypodermic needles 158, the needle capture assembly 118 represents a quick way to connect (disconnect) ninety-six hypodermic needles 158 or capillary tubes 114 and ninety-six syringe barrels 112 or reservoirs simultaneously.

FIG. 14 shows a perspective view of a detector block module 370 for holding linear arrays 140, 142 that comprise the upstream 136 and downstream 138 detector arrays, respectively. The detector block module 370, which is typically fabricated from a rigid material such as aluminum, has generally planar and parallel top 372 and bottom 374 surfaces and generally planar and parallel first 376 and second 378 sides. As noted in the description of FIG. 1, the upstream 136 and downstream 138 detector arrays monitor the volumetric flow rate of samples flowing through each syringe barrel 112 and capillary tube 114. The detector arrays 136, 138 are made up of twelve linear arrays 140, 142, each having eight detector elements spaced nine millimeters apart. The resulting twelve-by-eight or ninety-six-element detector arrays 136, 138 allow the set of syringes 108 to have the same lateral spacing as a standard ninety-six well microtiter plate. Each of the detector elements is comprised of an infrared emitter and an infrared detector, which are aligned on opposing sides of each syringe barrel 112. A useful IR emitter and detector include an IR LED and an IR-sensitive phototransistor, respectively. Note that the use of an infrared emitter and detector helps reduce interference from ambient visible light.

Thus, as shown in FIG. 14, the detector block module 370 includes eight through-bores 380 that extend from the top surface 372 to the bottom surface 374 of the block module 370. Each of the through-bores 380 has a diameter large enough to accommodate a syringe barrel 112. The detector block module 370 also includes pairs of rectangular notches 382, 384 cut into the first 376 and second 378 sides of the block 370. The pairs of rectangular notches 382, 384 are sized to contain components of a detector array element 386, which as noted above, comprise an infrared detector 388 and an infrared emitter 390. Each pair of rectangular notches 382, 384 includes first 392 and second 394 apertures that provide a line of sight between the IR detector 388 and IR emitter 390, respectively. In addition, the detector block module 370 includes clearance holes 396 that are located adjacent to the front 398 and rear 400 ends of the module 370. Each of the clearance holes 396 extends from the first 376 side to the second 378 side of the detector block module 370 and has a diameter large enough to allow a support rod (not shown) to pass through. To form each of the ninety-six element detector arrays 136, 138, twelve of the detector block modules 370 are stacked on support rods inserted through the clearance holes 396.

A suitable IR emitter 390 and an IR detector 388 are available from Honeywell under the trade designations SEP8706 and SDP8371, respectively. Since commercially available infrared emitters and detectors often emit or detect light over a larger range of angles than is desirable for detection of the liquid meniscus, this angular range may be reduced by partially blocking the entrance and exit apertures of these devices through the application of an opaque coating such as an enamel paint containing colloidal silver particles, or by the placement of an appropriately sized metal washer over the aperture.

As noted in the description of FIG. 1, the upstream 136 and downstream 138 detector arrays monitor the volumetric flow rate of fluid samples. The detector arrays 136, 138 measure the time necessary for a liquid meniscus within the syringe barrel 112 to travel between the detector arrays 136, 138, which can be accomplished by noting changes in voltages generated by the detector arrays 136, 138 in response to fluid characteristics. For example, in the absence of liquid in the barrel 112, infrared light from the emitter 390 exits the second aperture 394 of the detector block module 370, travels through the syringe barrel 112, enters the first aperture 392, and strikes the infrared detector 388. This results in a voltage, $V_S$, at the output of the detector 388. When the boundary between the fluid sample and air within the syringe barrel 112 passes the detector array element 386, $V_S$ changes relative to some reference voltage, $V_{REF}$. If the fluid sample is substantially transparent to infrared light, the change is brief and results from disruption of the infrared light beam by the sample meniscus. If, however, the fluid sample is opaque, $V_S$ exhibits a step change—an increase or decrease relative to $V_{REF}$—upon passage of the meniscus depending on the electrical response of the detector 388 to an increase in light level.

In a closely related embodiment, the apertures 392, 394 are not necessarily aligned. Infrared light from the emitter 390 exits the second aperture 394 of the detector block module 370, and enters the syringe barrel 112 interior. When the angular distribution of light from the emitter 390 is sufficiently broad, a portion of this light will reflect back into the barrel 112 at the interfaces between the barrel 112 and either the ambient air or barrel 112 contents. The reflected light will then travel around the barrel 112 interior, undergoing multiple reflections at its internal and external surfaces. Some fraction of light will escape from the barrel 112 each time the light is partially reflected from these surfaces. For reflections occurring near the first aperture 392, light escaping the barrel 112 will strike the infrared detector 388, producing voltage $V_S$ at the output of the detector 388. The fraction of light escaping the barrel 112 depends on the relative refractive index of the syringe barrel 112 and its contents, and therefore the magnitude of $V_S$ will depend on whether sample fluid coats the inner surface of the barrel 112 adjacent the detector array element 386. Therefore, the detector 338 output voltage, $V_S$, will exhibit a significant change relative to $V_{REF}$ upon passage of the fluid meniscus.

Although one can detect the transition in $V_S$ directly, the viscometer 100 typically employs either a standard comparator circuit or a Schmitt trigger circuit to detect a rise (or fall) in $V_S$. With a standard comparator, the comparator output, $V_O$, saturates at $V_{CC}$ for $V_S$ greater than $V_{REF}$ and saturates at $-V_{EE}$ for $V_S$ less than $V_{REF}$. Thus, when using the standard comparator, the momentary drop in $V_S$ results in a sharp decrease in $V_O$ from $V_{CC}$ to $-V_{EE}$ and a sharp increase in $V_O$ from $-V_{EE}$ to $V_{CC}$ as the meniscus passes the detector array element 386. The standard comparator usually works well unless $V_S$ is "noisy." Sources of noise include gas occlusions, voids, and other impurities in the fluid sample, which can perturb the IR light and result in spurious beam interruptions.

The Schmitt trigger circuit can detect the transition even for "noisy" $V_S$. It uses a comparator whose reference voltage, $V_{REF}$, is derived from a voltage divider across the output (i.e., positive feedback). $V_{REF}$ changes when the output switches state: $V_{REF}=\beta V_{CC}$ for $V_O>0$ and $-\beta V_{EE}$ for $V_O<0$, where $\beta$ is called the feedback factor and is a positive number less than unity. Thus, when $V_S$ rises through $V_{REF}=\beta V_{CC}$, $V_O$ is at $V_{CC}$ and switches to $-V_{EE}$, and when $V_S$ falls through $V_{REF}=-\beta V_{EE}$, $V_O$ is at $-V_{EE}$ and switches to $V_{CC}$. As a result, the Schmitt trigger will not respond to input noise having a magnitude less than the differences between the two threshold voltages, $V_N<\beta(V_{CC}+V_{EE})$. Note that one may implement the standard comparator and Schmitt trigger circuits in hardware or software.

One can use many different methods to determine the drop time, $\Delta t$, which is the time it takes for a liquid meniscus to travel between the detector arrays 136, 138. In a first method, the upstream and down stream detectors of a particular syringe barrel 112 are separately connected to an A/D board, which records $V_O$ (or $V_S$) at a predetermined sampling rate, r. A computer can search the recorded data streams for $V_O$ transitions (pulses) that indicate the passing of the meniscus. Assuming that r is the same for the upstream and downstream detectors, the computer can then calculate $\Delta t$ by dividing the number of data points acquired between the two pulses by the data acquisition rate. In a second method, the upstream and down stream detectors are connected to the A/D board, which records the voltage drop across both detectors in a single channel. Again, a computer can search the recorded data stream for the $V_O$ ($V_S$) transitions and calculate $\Delta t$. Alternatively, one can employ a timer on the A/D board, which is triggered by $V_O$ transitions, to measure the elapsed time directly.

FIG. 15 shows a top view of an optional needle alignment block 420. The needle alignment block 420 is typically fabricated from a rigid material such as aluminum, and can be attached to the rigid frame 102 that supports the parallel viscometer 100 (FIG. 1). The needle alignment block 420 includes through-holes 422 that extend from an upper surface 424 of the block 420 to a lower surface (not shown) of the block 420. The through-holes 422 are arrayed on nine-mm centers corresponding to the well spacing of a standard ninety-six well microtiter plate, and have diameters that allow passage of the capillary tube 114 portion of the syringe needles 158 (FIG. 2). Placing the needle alignment block 420 adjacent the tips 156 of the capillary tubes 114 ensures that the tubes 114 have uniform lateral spacing throughout their lengths.

Viscosity Measurement

To perform a measurement with the parallel viscometer 100 (FIG. 1), a DC motor (not shown) drives the plunger plate 120 towards the barrel retaining plate 116 until the tip 198 of each plunger 110 rests against the Luer tip 162 of each syringe barrel 112 (FIG. 3). A laboratory jack located adjacent the viscometer base 104 positions a ninety-six well microtiter plate (or similar vessel array) below the syringes 108 so that the tip 156 of each capillary tube 114 is immersed in a fluid sample within a particular well or vessel. The DC motor then drives the plunger plate 120 away from the barrel retaining plate 116, generating a vacuum between the plunger tip 198 and the capillary tip 156, which aspirates fluid sample into each syringe barrel 112. Once the plunger tip 198 passes the vent hole 168, the interior of each syringe barrel 112 returns to atmospheric pressure and fluid sample begins to drain from the barrel 112 through the capillary tube 114. As noted when describing FIG. 14, the upstream 136 and downstream 138 detector arrays monitor the volumetric flow rate of the fluid samples by measuring the time it takes for the liquid meniscus within each syringe barrel 112 to travel between the detector arrays 136, 138. When the boundary between the fluid sample and air within each syringe barrel 112 passes a detector array element 386, the meniscus disrupts the beam from the IR emitter 390, which produces a brief signal at the IR detector 388. Generally, the length and diameter of the capillary tube 114 are chosen to achieve a reasonable drop time for the fluid samples, typically from about ten to sixty seconds. In addition, each plunger 110 is withdrawn from the syringe barrel 112 at a rate such that the meniscus is above the upstream 136 detector array element 386 by the time the plunger tip 198 passes the vent hole 168.

As noted in the overview section, one can calculate viscosity, $\eta$, from the volumetric flow rate, Q. of samples flowing through the capillary tubes 114 using the Hagen-Poiseulle equation:

$$Q = \frac{\pi d^4 \Delta P}{128 l \eta} \qquad \text{I}$$

where d and l are the inner diameter and length of the capillary tube 114, and $\Delta P$ is the pressure drop across l. For gravity-driven flows, the pressure drop is the product of the fluid sample density, the gravitational acceleration, and l. Q can be calculated from the expression:

$$Q = \frac{\pi D^2 L/4}{\Delta t} \qquad \text{II}$$

where D is the inner diameter of the syringe barrel 112, L is the distance between the upstream 136 and downstream 138 detector arrays and $\Delta t$ is the measured drop time.

In another embodiment, the viscometers described above can be operated by creating a vacuum in the reservoirs (e.g., the barrels). The vacuum can be created by a pump or by rapidly withdrawing the plunger through the barrel. A pressure sensor can be used to monitor the pressure of the vacuum created. The flow of the fluid to be measured into the viscometer can be monitored by monitoring the pressure. For example if the plunger is pulled back a fixed distance extremely rapidly, the time for the liquid to flow into the line may be monitored. The pressure may initially drops rapidly as the dead volume is expanded, and recovers as liquid flows into the tube and reduces the dead volume. Information on the fluid flow rate and viscosity can be derived from the pressure vs. time curves for the fluid. One method for using this embodiment comprises a method for rapidly determining the viscosity of liquids comprising filling at least a part of the reservoir and/or tube with a compressible fluid (e.g. air); inserting the tube into the material to be sampled; retracting the syringe plunger at a specified rate for a specified time; measuring the pressure in the line during and after the retraction of the syringe pump plunger; calculating the trapped air volume between the rising liquid meniscus in the tube and/or reservoir and the syringe pump plunger, as a function of time, from the measured pressure within this volume as sensed by the pressure sensor; calculating the volume of liquid which has been aspirated into the pipette tip and line, as a function of time, from the calculated trapped air volume and knowledge of the displacement of the syringe pump plunger; and calculating a viscosity of the liquid from the observed liquid flow rate in response to the measured pressure. Those of skill in the art will appreciate that this is only one method for using this embodiment and other methods will be evident upon review of this specification.

Molecular Weight Measurement

One can use viscosity measurements to estimate molecular weights of polymers in solution. For a polymer dissolved in a solvent, the ratio of the polymer solution viscosity, $\eta$, to the solvent viscosity, $\eta_S$, is proportional to the concentration of the polymer, C, as the concentration approaches infinite dilution (limit of C equals zero):

$$\eta/\eta_S = 1 + C[\eta] \qquad \text{III}$$

In equation III, $[\eta]$ is the intrinsic viscosity, which exhibits a power-law dependence on polymer molecular weight given by the Mark-Houwink-Sakurada (MHS) relation, $$[\eta] = [\eta_O] M^\alpha \qquad \text{IV}$$

where the constants $[\eta_O]$ and $\alpha$ depend on the polymer, solvent, and temperature. Correction factors are available in the literature for solutions containing a distribution of polymer molecular weights.

To measure the molecular weight of a polymer in solution using the parallel viscometer 100, one measures the drop time, $\Delta t_S$, for the solvent and then measures $\Delta t$ for the polymer solution. Since the drop time is inversely proportional to the volumetric flow rate, Q, through the capillary tube 114, and Q is inversely proportional to the viscosity of the solvent and the polymer solution, the ratio $\eta/\eta_S$ is equal to the ratio of the drop times, $\Delta t/\Delta t_S$. Because corrections associated with the dimensions of the instrument, changes in the height of the liquid sample in the reservoir, and transitions in flow behavior at the entrance and exit of the capillary tube 114 are similar for $\Delta t$ and $\Delta t_S$ measurements, the measurement of $\eta/\eta_S$ is self-normalizing. If C is known, one can determine the intrinsic viscosity from equation III, and the molecular weight from equation IV (MHS relation).

If the concentration of the polymer solution is initially unknown, both the molecular weight and the concentration can be estimated by measuring the ratio of drop times in two different solvents. The first solvent is a good solvent for the polymer, and typically has a constant $\alpha$ of 0.7 or greater. The second solvent is a marginal solvent for the polymer, and is usually prepared by adding a known amount of a poor solvent to the first solvent. Ordinarily, one should maximize the difference in $\alpha$ between the first (good) and second (marginal) solvents by adding as much of the poor solvent as possible to the first solvent without causing the polymer to precipitate. In such cases, the marginal solvent typically has an $\alpha$ of about 0.5. If we then define $\mu = \eta/\eta_S - 1$, where $\eta/\eta_S$ is the ratio of drop times as described above, then $$\frac{\mu_1}{\mu_2} = \frac{C_1[\eta_1]}{C_2[\eta_2]} = \left(\frac{C_1}{C_2}\right)\left(\frac{\eta_{O,1}}{\eta_{O,1}}\right)M^{\alpha_1 - \alpha_2} \qquad \text{V}$$

where subscripts 1 and 2 denote measurements of polymer solutions made using the first and second solvents, respectively, and the second solvent is prepared by adding a known amount of a poor solvent to the first solvent.

In equation V, the constants $[\eta_{O,1}]$, $[\eta_{O,2}]$, $\alpha_1$, and $\alpha_2$ are determined by measurements of polymer standards at known concentrations prior to measurements of the unknown solution. Since the ratio of $C_1$ to $C_2$ is known, the ratio $\mu_1/\mu_2$ depends only on the molecular weight of the polymer. After estimating the molecular weight via this method, either concentration ($C_1$ or $C_2$) can be estimated from the MHS relation for the polymer of interest in solvent 1 or 2.

Modifications

The parallel viscometer shown in FIG. 1 can be modified to screen high viscosity liquids such as polymer melts. A force sensor is attached to the top of each plunger 110. After filling each syringe barrel 112 with high viscosity liquids, the plunger 110 descends at a constant rate and the force sensor determines the force required to maintain this motion. Assuming negligible friction between the plunger 110 and the barrel 112, the force is roughly proportional to the pressure inside the barrel 112; in combination with the flow rate through the capillary tube 114, the viscosity of each liquid can be determined using the Hagen-Poiseulle relation (equation I). If the liquid is relatively incompressible, the flow rate may be inferred from the rate at which the plunger 110 descends. Thus, optical detectors 386 are not required for measurement of flow rate, which permits the syringe barrel 112 to be made of a strong, opaque material such as stainless steel. In an alternate embodiment, each plunger is independently attached to a weight, which in turn is held in place by an electromagnet or mechanical latch. A measurement is conducted by releasing the weight and either permitting the plunger 110 to descend for a fixed amount of time while measuring the quantity of material expelled from the capillary 114 (for example, by weighing or noting the total travel distance of the plunger), or by measuring the amount of time it takes the plunger 110 to descend a fixed distance.

EXAMPLES

The following examples are intended to be illustrative and non-limiting, and represent specific embodiments of the present invention.

Example 1

Variation in Drop Time Between Syringes

Figure 16:
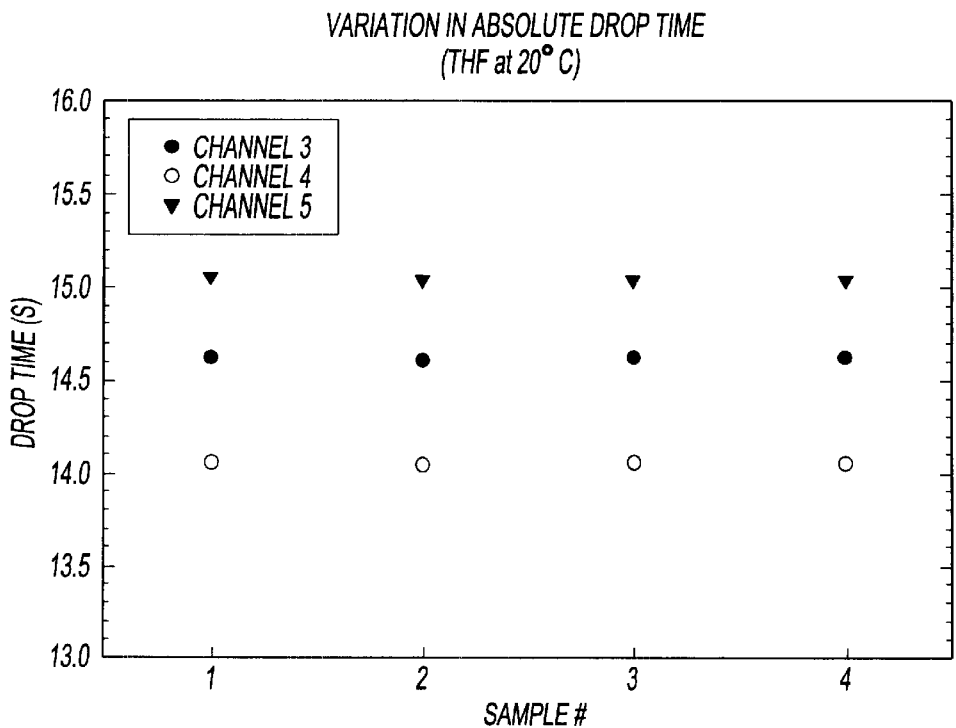
FIG. 16 shows a plot of drop time versus sample number.

A parallel viscometer similar to the apparatus depicted in FIG. 1 was used to measure drop time, $\Delta t$, for tetrahydrofuran (THF) samples at 20° C. The drop time was measured for ninety-six samples simultaneously, and was repeated four times for each sample. FIG. 16 plots drop time (in seconds) versus sample number (1–4) that were obtained for three different syringes (channels 3, 4 and 5). Although some variation exists between syringes (channels), drop time measurements for individual channels are highly repeatable.

Example 2

Single Channel (Syringe) Reproducibility

Figure 17:
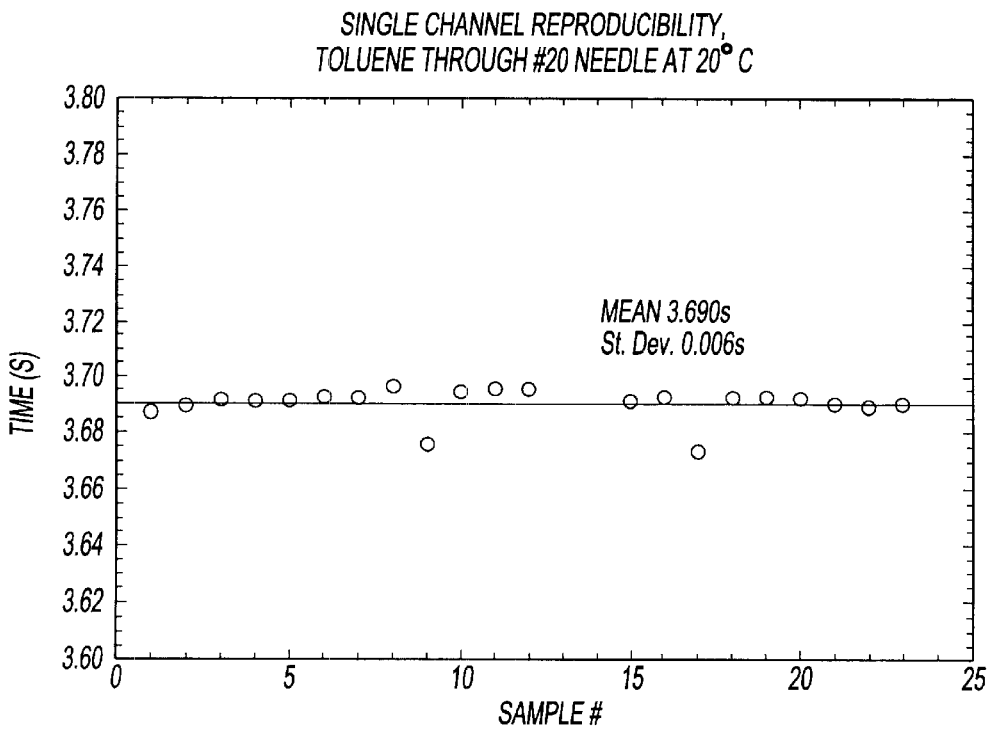
FIG. 17 shows a plot of drop time versus twenty-three samples for a single syringe.

The parallel viscometer of Example 1 was used to measure drop time for toluene samples at 20° C. The drop time was measured for a series of twenty-three samples using a single syringe (channel) having a 20-gauge hypodermic needle. FIG. 17 plots drop time (in seconds) versus sample number (1–23) for the single channel. The average drop time for the twenty-three samples was 3.690 s, and the standard deviation was 0.006 seconds. Note that a filter could be used to eliminate disordant data (sample 9, 17).

Example 3
Measurement of Intrinsic Viscosity

Figure 18:
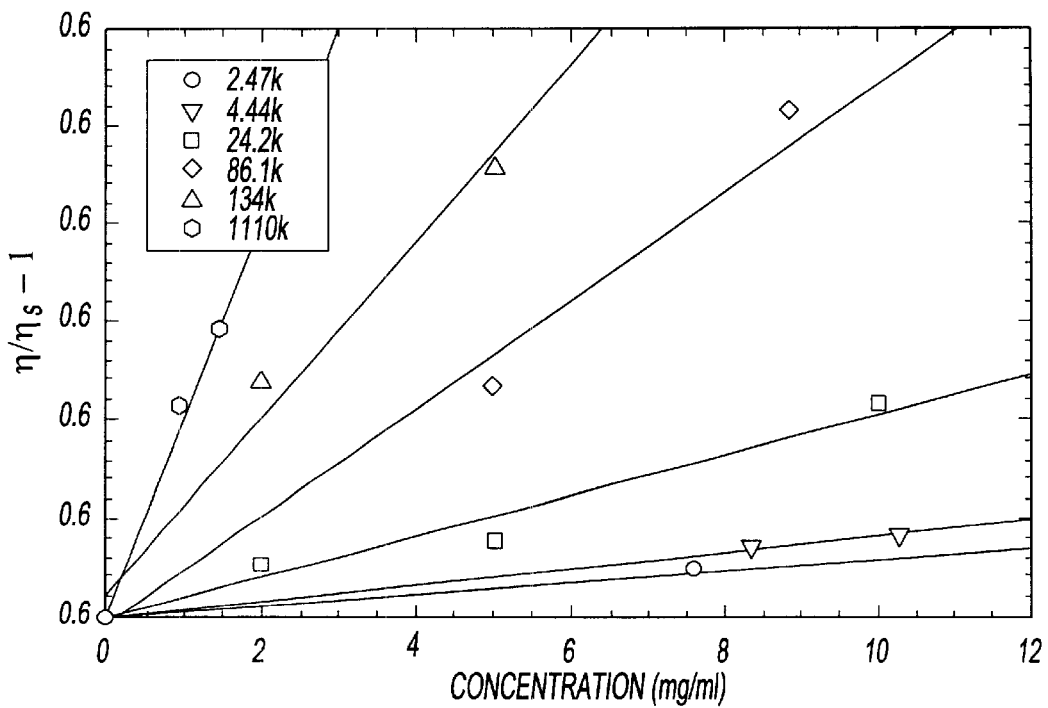
FIG. 18 shows a plot of relative viscosity—1 versus concentration of polyisobutylene in hexane for six narrow molecular weight distribution polyisobutylene standards.
Figure 19:
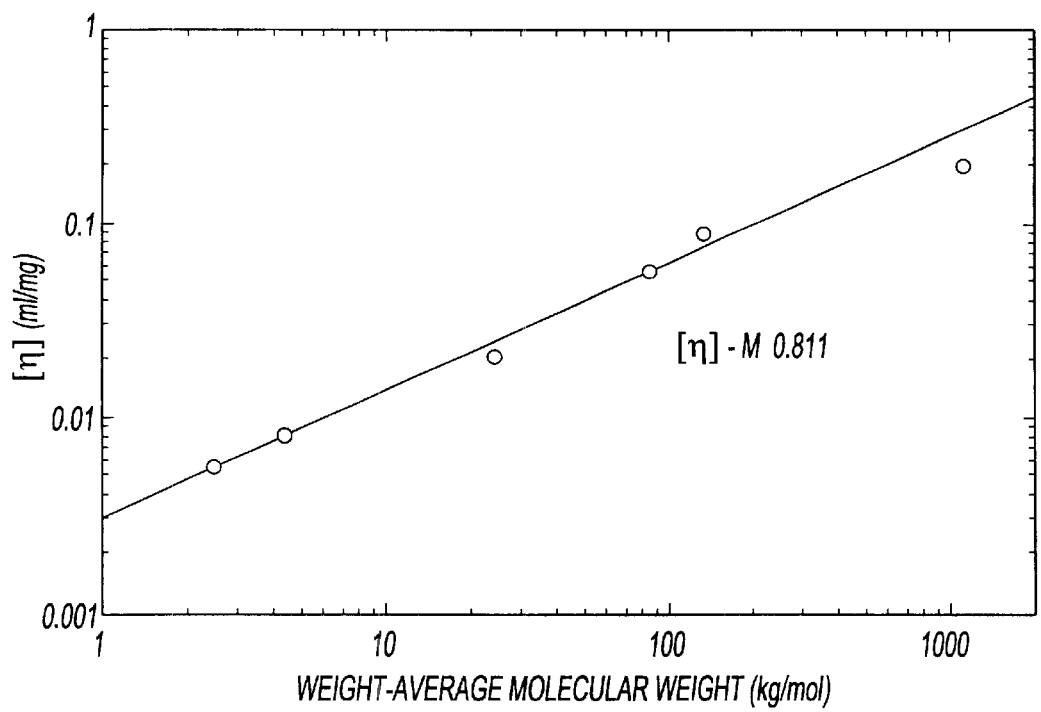
FIG. 19 shows a plot of intrinsic viscosity versus weight average molecular weight for narrow molecular weight distribution polyisobutylene standards.

The parallel viscometer of Example 1 and 2 was used to determine the intrinsic viscosities of a set of commercially available polyisobutylene standards at concentrations in hexane from 1 to 20 mg/ml at 25° C. The molecular weights of these materials as reported by the supplier (Polymer Standards Service USA, Silver Springs, Md.) appear in Table 1. FIG. 18 shows $\Delta t/\Delta t_S-1$ or $\eta/\eta_S-1$ versus polyisobutylene concentration, where $\Delta t$ and $\Delta t_S$ are the drop times for the polymer solution and for pure hexane, respectively, and where the ratio $\eta/\eta_S$ is the relative viscosity. Each data point represents an average of at least five measurements. A linear least-squares fit each of these curves yields the intrinsic viscosity, $[\eta]$, for each standard of differing molecular weight. These data are summarized in Table 1 and plotted in FIG. 19. The resulting power law relation, $[\eta] \sim M^{0.611}$, indicates that hexane is a reasonable (though not good ) solvent for this polymer.

TABLE 1

Weight-average molecular weights ($M_w$), number-average molecular weights ($M_n$), and intrinsic viscosities ($[\eta]$) for polyisobutylene standards

| $M_w$ (g/mol) | $M_n$ (g/mol) | $[\eta]$ (ml/mg) $\times 10^3$ |
|---|---|---|
| 2470 | 2200 | 5.65 |
| 4400 | 3200 | 8.05 |
| 24200 | 19600 | 21.0 |
| 86100 | 72100 | 53.3 |
| 134000 | 117000 | 89.0 |
| 1110000 | 862000 | 201 |

It is understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. An apparatus for measuring viscosity or related properties of fluid samples in parallel, the apparatus comprising:
   a frame;
   a plurality of tubes, each having a first end and second end, providing flow paths for the fluid samples, each of the tubes having a predefined length terminating at the first end with a tip adapted for aspirating a sample from a sample holder and a substantially uniform inner diameter over at least a portion of the pre-defined length;
   a plurality of reservoirs each in fluid communication with one of the plurality of tubes, and being connected therewith via a hub;
   an assembly attached to the frame adapted for receiving said tubes and securing them in place relative to the frame;
   a mechanism adapted for filling the reservoirs with the fluid samples; and
   a device adapted for determining volumetric flow rates of fluid samples flowing from the reservoirs and through the plurality of tubes simultaneously;
   wherein the apparatus is capable of measuring viscosity of related properties of at least five fluid samples simultaneously.

2. The apparatus of claim 1, wherein the mechanism for filling the reservoirs is a vacuum source in fluid communication with the reservoirs.

3. The apparatus of claim 1, wherein the mechanism for filling the reservoirs is a single or multiple-channel pipette.

4. The apparatus of claim 1, wherein the device for determining volumetric flow rate comprises sensors located at upstream and downstream positions along each of the reservoirs.

5. The apparatus of claim 4, wherein each of the sensors comprises a light source and a light detector, the light detector generating a signal in response to a momentary interruption of light from the light source.

6. The apparatus of claim 5, wherein the light source is an infrared emitter and the light detector is an infrared detector.

7. The apparatus of claim 6, wherein the infrared emitter is an LED and the infrared detector is an IR-sensitive phototransistor.

8. The apparatus of claim 5, wherein the light detector includes a Schmitt trigger circuit.

9. The apparatus of claim 1 further comprising a plunger for each tube.

10. The apparatus of claim 9 further comprising a plunger plate for providing uniform translation of a plurality of plungers.

11. The apparatus of claim 10, further comprising a DC motor mounted on the frame for axially driving the plunger plate.

12. The apparatus of claim 11 wherein the plunger plate is axially driven by a rotatable driveshaft having a stationary axis.

13. The apparatus of claim 10 wherein the device is an infrared detector device.

14. The apparatus of claim 13 wherein each reservoir has a vent hole located upstream of the infrared detector device for providing fluid communication with atmosphere and for providing a vacuum break.

15. The apparatus of claim 1, wherein the apparatus is capable of measuring viscosity or related properties of at least twelve fluid samples simultaneously.

16. The apparatus of claim 1, wherein the apparatus is capable of measuring viscosity or related properties of at least forty-eight fluid samples simultaneously.

17. The apparatus of claim 1, wherein the apparatus is capable of measuring viscosity or related properties of at least ninety-six fluid samples simultaneously.

18. The apparatus of claim 1, further comprising receptacles for collecting fluid samples exiting the tubes.

19. The apparatus of claim 18, wherein the receptacles are wells of a microtiter plate.

20. The apparatus of claim 1, further comprising an environmental chamber surrounding the tubes and reservoirs for maintaining the fluid samples are a constant temperature.

21. The apparatus of claim 1 wherein the hub is a luer hub.

22. The apparatus of claim 21, wherein said assembly is a needle capture assembly that includes a hub capture plate having through holes therein adapted for matingly receiving the hub and to which is attached to a preloaded block having a plurality of through holes adapted for permitting penetration through of the tubes.

23. The apparatus of claim 22, wherein the preloaded block includes a plurality of through holes that are arranged to correspond with the well spacing of a microtiter plate.

24. The apparatus of claim 23, wherein the preloaded block includes an 8×12 array of throughholes.

25. The apparatus of claim 22, wherein the hub has an enlarged flanged head portion spaced apart from an enlarged body portion by a neck.

26. The apparatus of claim 25, wherein the throughholes of hub capture plate are defined to include a first upstream portion that has a width smaller than the flanged head portion and the enlarged body portion of the hub for receiving the rest of the hub and resisting axial movement of the hub.

27. The apparatus of claim 26 further comprising a spring disposed in the preload block for applying a force against the hub.

28. An apparatus for measuring viscosity or related properties of a plurality of fluid samples, the apparatus comprising:
   a three axis robot having at least one arm and at least one tip on the at least one arm;
   a tube providing a flow path for the plurality of fluid samples, the tube having a predefined length and a substantially uniform inner diameter over at least a portion of the pre-defined length;
   a syringe barrel defining a reservoir for receiving the fluid samples, the reservoir in fluid communication with the tube, the barrel and the tube attached to the at least one tip of the robot and the barrel including a vent hole providing fluid communication between the reservoir and the atmosphere outside the barrel;
   a plunger disposed within the barrel for aspirating the plurality of fluid samples into the reservoir, the plunger aspirating each the plurality of samples into the reservoir until the plunger passes the vent hole, which then allows each of the plurality of samples to flow out of the reservoir; and
   an upstream detector and a downstream detector for detecting the plurality of samples as the plurality of samples flows out of the reservoir such that a volumetric flow rate of each of the plurality of fluid samples can be determined;
   wherein the apparatus is capable of measuring the viscosity or related properties of the plurality of fluid samples by relating the volumetric flow rate of each of the plurality of samples to the viscosity or related properties as the robot moves the tube from sample to sample to aspirate each of the plurality of samples followed by allowing each of the plurality of samples to flow out of the reservoir.

29. An apparatus for measuring viscosity or related properties of a at least four fluid samples, the apparatus comprising;
   a three axis robot having at least one arm and at least two tips on the at least one arm;
   at least two tubes providing a at least two flow paths for the at least four fluid samples, the at least two tubes having a predefined length and a substantially uniform inner diameter over at least a portion of the pre-defined length;
   at least two syringe barrels defining at least two reservoirs for receiving the at least four fluid samples, the at least two reservoirs in fluid communication with the at least two tubes, the at least two barrels and the at least two tubes attached to the at least two tips of the robot and the at least two barrels including at least two vent holes for providing fluid communication between the at least two reservoirs and the atmosphere outside the at least two barrels;
   at least two plungers disposed within the at least two barrels for aspirating the at least four fluid samples into the at least two reservoirs, the at least two plungers aspirating the at least four samples into the at least two reservoirs until the at least two plungers pass the at least two vent holes, which then allows each of the at least four samples to flow out of the at least two reservoirs; and
   a plunger plate connect to the at least two plungers, the plunger plate providing uniform translation of the at least two plungers for aspirating the at least four samples
   an upstream detector and a downstream detector associated with the at least two reservoirs for detecting the at least four samples as the at least four samples flow out of the at least two reservoirs such that a volumetric flow rate of each of the at least four samples can be determined;
   wherein the apparatus is capable of measuring the viscosity or related properties of the at least four fluid samples by relating the volumetric flow rate of each of the at least four samples to the viscosity or related properties as the robot moves the at least two tubes from sample to sample to aspirate each of the at least four samples followed by allowing each of the at least four samples to flow out of the reservoir.

30. A method of screening fluid samples comprising:
   providing a plurality of fluid samples to a plurality of wells;
   providing a plurality of reservoirs in fluid communication with the plurality of fluid samples, the reservoirs defined by a plurality of barrels, the barrels attached to a plurality of capillary tubes via a plurality of hubs;
   aspirating the plurality of fluid samples into the plurality of reservoirs using vacuum pressure to induce flow of the plurality of samples through the plurality of capillary tubes and through the plurality of hubs;
   allowing the plurality of fluid samples to flow from the reservoirs through the plurality of tubes, the tubes having known diameter and length, the tubes secured in place by an assembly that is adapted to receive the tubes, the assembly being attached to a frame; and
   detecting the volumetric flow rates of the plurality of fluid samples through each of the tubes simultaneously; and
   relating the volumetric flow rates to a rheological property of the plurality of fluid samples.

31. The method of claim 30, wherein providing fluid samples to the plurality of reservoirs comprises aspirating the fluid samples into the reservoirs.

32. The method of claim 31, wherein detecting the volumetric flow rates comprises measuring times required for a meniscus within each of the reservoirs to travel a predetermined distance.

33. The method of claim 32, further comprising computing the volumetric flow rates from the meniscus travel times.

34. The method of claim 33, further comprising computing viscosities for each of the fluid samples from the meniscus travel times.

35. The method of claim 33, further comprising estimating molecular weights of the fluid samples from the meniscus travel times.

36. The method of claim 31, further comprising detecting the volumetric flow rates of at least twelve of the fluid samples through each of the tubes simultaneously.

37. The apparatus of claim 31, further comprising detecting the volumetric flow rates of at least forty-eight of the fluid samples through each of the tubes simultaneously.

38. The apparatus of claim 31, further comprising detecting the volumetric flow rates of at least ninety-six of the fluid samples through each of the tubes simultaneously.

39. An apparatus for measuring viscosity or related properties of a plurality of fluid samples, the apparatus comprising:

a three axis robot having at least one arm and at least one tip on said at least one arm;

a tube providing a flow path for the plurality of fluid samples, the tube having a predefined length and a substantially uniform inner diameter over at least a portion of the pre-defined length;

a reservoir for containing the fluid samples, the reservoir in fluid communication with the tube via a hub and said reservoir attached to said at least one tip of said robot;

an array of fluid samples from wells of a substrate housing;

a mechanism for aspirating the plurality of fluid samples into the reservoir from the array of fluid samples; and a pair of detectors for determining volumetric flow rates of the plurality of fluid samples flowing from the reservoir and through the tube, the pair of detectors determining the volumetric flow rates by detecting the plurality of fluid samples at the plurality of samples flow out of the reservoir after aspiration;

wherein the 3 axis robot arm is adapted for translation between the wells of the substrate for measuring viscosity or related properties of the plurality of fluid samples by said robot moving said tube from sample to sample in the array of samples.

40. The apparatus of claim 29, wherein said robot comprises at least 2 tips with a reservoir attached to each of said at least 2 tips.

41. The apparatus of claim 40, wherein said robot comprises at least 2 arms, with each of said arms comprising at least one tip with said reservoir.

42. The apparatus of claim 39 further comprising a second robot arm with a second tip wherein at least two viscometers are placed on the tips of the robot arm.

43. The apparatus of claim 39 wherein the reservoir is defined by a barrel and an outer diameter of the tip is larger than an inner diameter of the barrel.

44. The apparatus of claim 39 wherein the apparatus is capable of measuring the viscosity or related properties of the plurality of fluid samples at a rate of no greater than 60 second per sample.

45. The apparatus of claim 39 wherein the array of fluid samples is an array of synthetic samples.

46. The apparatus of claim 45 wherein the array of fluid samples is an array of polymer materials.

47. An apparatus for measuring viscosity or related properties of fluid samples in parallel, the apparatus comprising:

an array of syringes, each of the syringes comprising a barrel for containing the fluid samples, a plunger located within the barrel for aspirating the fluid samples into the barrel, and a hypodermic needle in fluid communication with the barrel, the hypodermic needle providing a flow path for the fluid samples and having a substantially uniform inner diameter over a majority of its length; and upstream and downstream detector arrays located along the barrel of each syringe for monitoring volumetric flow rates of the fluid samples through each hypodermic needle simultaneously;

wherein the apparatus is capable of measuring viscosity or related properties of at least five fluid samples simultaneously.

48. The apparatus of claim 47, further comprising a plunger plate attached to each plunger, the plunger plate providing uniform translation of each plunger in a direction parallel to its longitudinal axis.

49. The apparatus of claim 48, further comprising a motor for driving the plunger plate, the motor mechanically linked to the plunger plate.

50. The apparatus of claim 49, further comprising a motor controller for regulating the speed and direction of the motor and the plunger plate.

51. The apparatus of claim 48, wherein the upstream and downstream detector arrays each comprise a plurality of detector elements, each of the detector elements comprising an infrared emitter and an infrared detector aligned on opposing sides of each syringe barrel, the infrared detector generating a signal in response to a momentary interruption of light from the infrared emitter.

52. The apparatus of claim 51, wherein the infrared detector includes a Schmitt trigger detector.

53. The apparatus of claim 47, wherein each barrel has a vent hole located upstream of the upstream detector array, the vent hole providing fluid communication between the barrel interior and the atmosphere and providing a vacuum break during withdraw of the plunger.

54. The apparatus of claim 47, wherein the apparatus is capable of measuring viscosity or related properties of at least twelve fluid samples simultaneously.

55. The apparatus of claim 47, wherein the apparatus is capable of measuring viscosity or related properties of at least forty-eight fluid samples simultaneously.

56. The apparatus of claim 47, wherein the apparatus is capable of measuring viscosity or related properties of at least ninety-six fluid samples simultaneously.

* * * * *

UNITED STATES PATENT AND TRADEMARK OFFICE
CERTIFICATE OF CORRECTION

PATENT NO. : 6,393,898 B1
DATED : May 28, 2002
INVENTOR(S) : Damian Hajduk et al.

It is certified that error appears in the above-identified patent and that said Letters Patent is hereby corrected as shown below:

Column 19,
Line 38, replace "29" with -- 39 --.

Signed and Sealed this

Seventeenth Day of December, 2002

JAMES E. ROGAN
*Director of the United States Patent and Trademark Office*